(12) United States Patent
Ono

(10) Patent No.: US 6,834,202 B2
(45) Date of Patent: Dec. 21, 2004

(54) BLOOD FLOW MEASURING APPARATUS

(75) Inventor: Shigeaki Ono, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 317 days.

(21) Appl. No.: 09/933,710

(22) Filed: Aug. 22, 2001

(65) Prior Publication Data
US 2001/0056239 A1 Dec. 27, 2001

Related U.S. Application Data

(62) Division of application No. 09/031,765, filed on Feb. 27, 1998, now Pat. No. 6,337,993.

(30) Foreign Application Priority Data

Feb. 27, 1997 (JP) ............................... 9-058590
Feb. 27, 1997 (JP) ............................... 9-058591
Feb. 28, 1997 (JP) ............................... 9-062497

(51) Int. Cl.$^7$ ................................ A61B 6/00
(52) U.S. Cl. .................. 600/476; 351/210; 351/221
(58) Field of Search ................... 600/310, 476; 351/205, 206, 221, 209, 210

(56) References Cited

U.S. PATENT DOCUMENTS

| 3,802,768 | A | | 4/1974 | Robinson et al. ............. 351/39 |
| 4,257,689 | A | | 3/1981 | Yancey ......................... 351/13 |
| 4,830,483 | A | | 5/1989 | Kohayakawa ............... 351/221 |
| 4,866,243 | A | | 9/1989 | Sakane et al. .............. 219/121 |
| 5,106,184 | A | * | 4/1992 | Millbocker ................. 351/221 |
| 5,125,730 | A | | 6/1992 | Taylor et al. ............... 351/206 |
| 5,186,173 | A | | 2/1993 | Zuckerman ................. 128/633 |
| 5,630,179 | A | | 5/1997 | Kishida ....................... 396/18 |
| 5,751,396 | A | | 5/1998 | Masuda et al. ............. 351/206 |
| 5,757,461 | A | | 5/1998 | Kasahara et al. ........... 351/206 |
| 5,844,658 | A | | 12/1998 | Kishida et al. ............. 351/206 |
| 5,894,337 | A | | 4/1999 | Okinishi et al. ............ 351/205 |
| 6,027,216 | A | | 2/2000 | Goyton et al. .............. 351/205 |
| 6,112,114 | A | | 8/2000 | Dreher ........................ 351/206 |
| 6,337,993 | B1 | * | 1/2002 | Kishida et al. ............. 600/476 |
| 6,535,757 | B2 | * | 3/2003 | Ono ............................ 600/476 |
| 2003/0071966 | A1 | * | 4/2003 | Matsumoto ................. 351/206 |

FOREIGN PATENT DOCUMENTS

| JP | 63-288133 | 11/1988 |
| JP | 7-31596 | 2/1995 |
| WO | WO 92/03084 | 3/1992 |

* cited by examiner

Primary Examiner—Shawna J. Shaw
(74) Attorney, Agent, or Firm—Fitzpatrick, Cella, Harper & Scinto

(57) ABSTRACT

A blood flow measuring apparatus includes a system control unit that sends outputs for controlling the start and end of the measurement to optimum gain calculation units, which calculate the optimum gains of photomultipliers for receiving the light reflected from the eye fundus and the system control unit controls whether the optimum gains are outputted or not. Also, the optimum gain calculation units respectively supply the system control unit with outputs for monitoring whether the setting of the optimum gain has been completed or not, whereby the system control unit discriminates whether the photomultipliers have been set at the optimum gains.

5 Claims, 20 Drawing Sheets

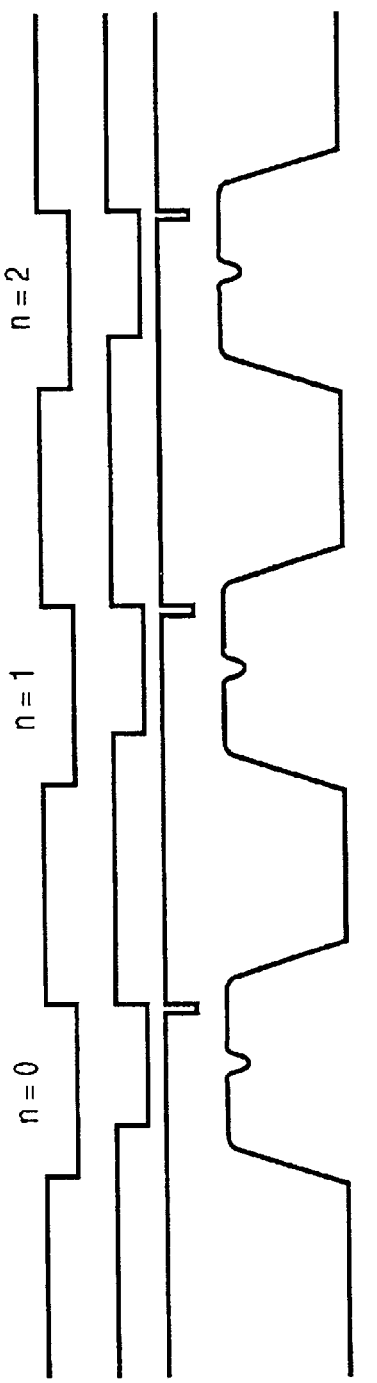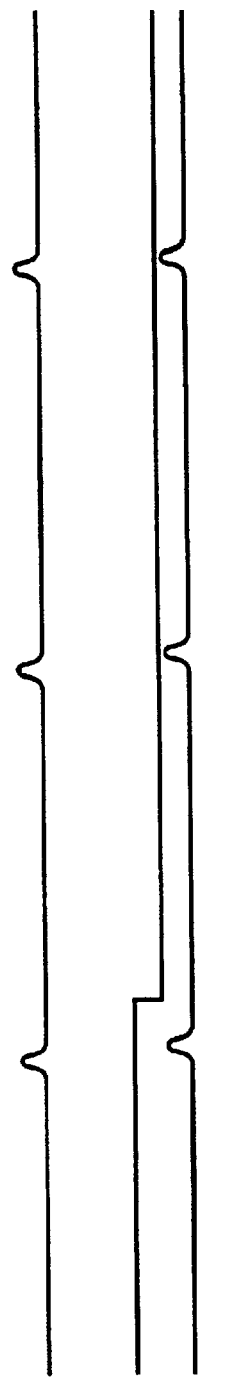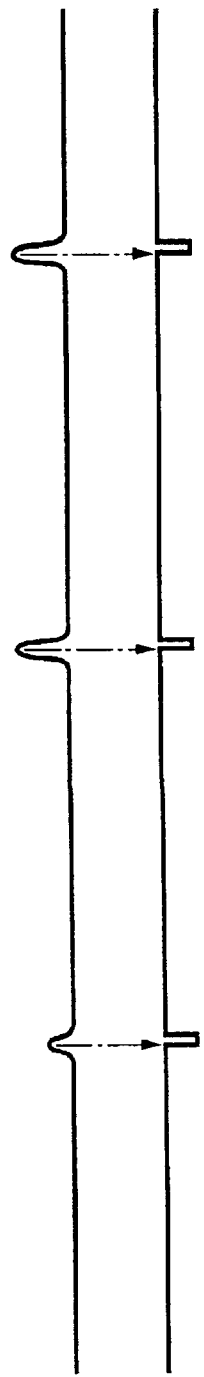
FIG. 18A
FIG. 18B
FIG. 18C
FIG. 18D
FIG. 18E
FIG. 18F
FIG. 18G
FIG. 18H
FIG. 18I

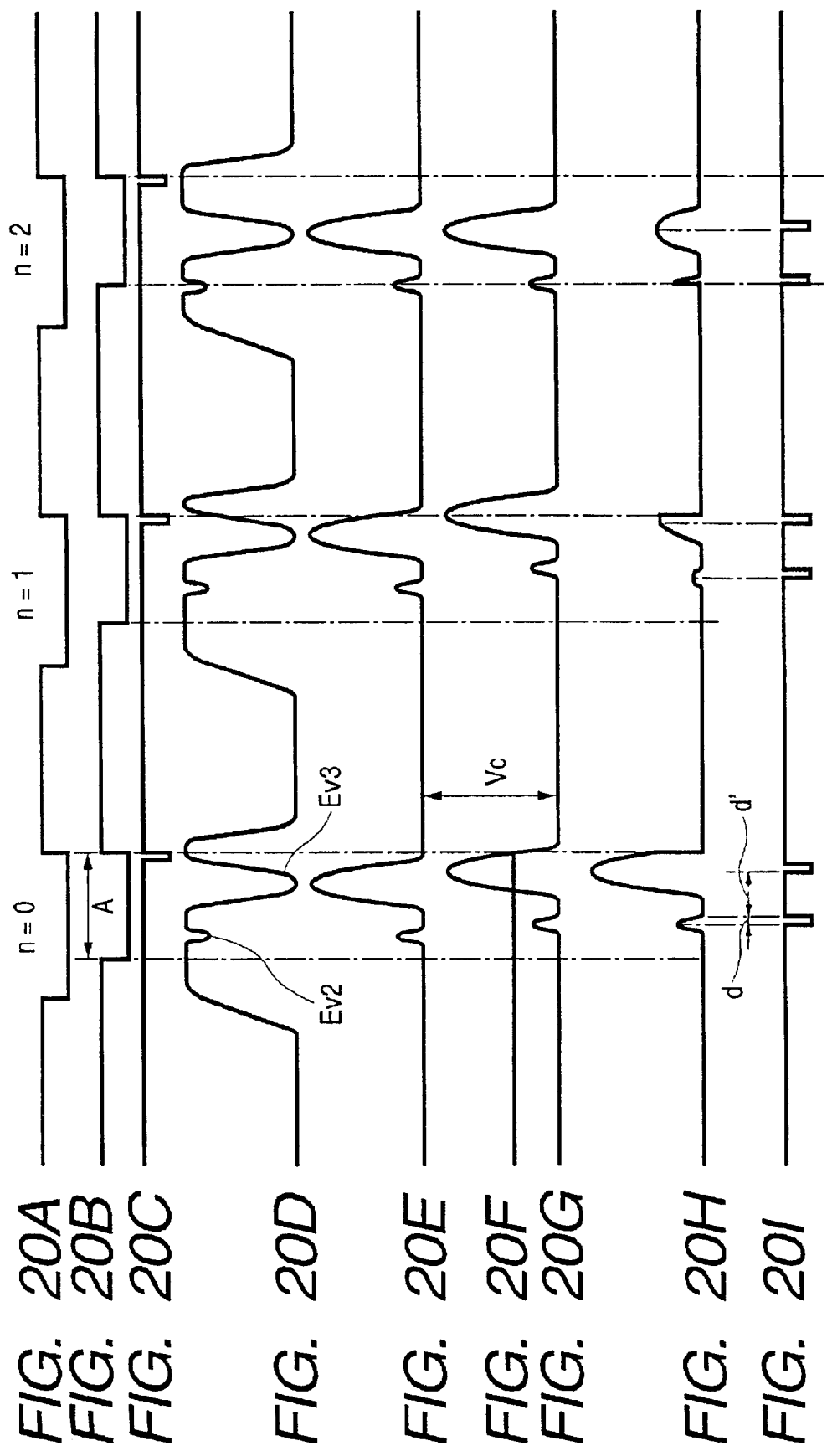

BLOOD FLOW MEASURING APPARATUS

This application is a division of U.S. patent application Ser. No. 09/031,765, filed Feb. 27, 1998, now U.S. Pat. No. 6,337,993 issued Jan. 8, 2002.

BACKGROUND OF THE INVENTION

1. Field of the Invention

The present invention relates to an eye fundus blood flow meter for measuring the blood flow velocity, etc., in the blood vessels of the fundus.

2. Related Background Art

There is already known a laser Doppler blood flow meter capable of tracking the vessel of the fundus of the eye to be examined and measuring the absolute blood flow velocity of the tracked vessel, and there is disclosed, for example in the Japanese Patent Laid-Open Application No. 7-031596, an apparatus for irradiating the vessel of the eye fundus with tracking laser light and laser light for measuring the blood flow velocity. In such an eye fundus blood flow meter, a reflected light, based on the laser light irradiating the eye fundus vessel for measuring the blood flow velocity and undergoing a Doppler shift caused by the blood cells flowing in the vessel, is received by a photomultiplier and the blood flow velocity is determined from the Doppler shift.

In such conventional apparatus, however, since the amount of the reflected light undergoing the Doppler shift varies significantly, for example, according to the position of the blood vessel on the eye fundus, the gain of the photomultiplier constituting the photosensor has to be adjusted frequently, each time the blood vessel to be measured is changed or the entering path of the measuring light is changed. For this reason, the eye to be examined is given an excessive amount of light by the operations of the examiner.

Also in the gain adjustment of the photomultiplier, the gain is adjusted to a maximum immediately before the start of the tracking operation since the received amount of light is very weak in this state, and, when the tracking operation is started, a large amount of light enters the photomultiplier at such a maximum gain, so that the deterioration of the photosensor is accelerated.

In the field of ophthalmic inspecting apparatus for tracking the movement of the blood vessels on the fundus of the eye to be examined, there are already known, for example, an apparatus for effecting two-dimensional tracking by detecting the vessel movement in two locations as disclosed in the Japanese Patent Laid-Open Application No. 63-288133, and an apparatus for effecting one-dimensional tracking by detecting, in one location, movement perpendicular to the direction of the blood vessel, as disclosed in the Japanese Patent Laid-Open Application No. 6-503733.

In such ophthalmic inspecting apparatus, a one-dimensional CCD is employed as the photosensor means for receiving the tracking light reflected on the eye fundus, and the tracking operation is achieved by calculating the amount of deviation between the tracking center position and the image position of the blood vessel by processing a signal indicating the blood vessel image. In such operation, in order to optimize the level of the blood vessel image signal, the gain of an amplifier is electrically regulated either manually or automatically, or the gain of an image intensifier positioned in front of the one dimensional CCD is regulated in a similar manner to adjust the amount of light entering the one-dimensional CCD, in such a manner that the output signal level thereof lies within a predetermined range.

There is furthermore proposed an apparatus capable of tracking a moving object, by detecting the position thereof relative to a one-dimensional CCD and executing continuous feedback of the obtained position signal to image taking direction varying means which varies the image taking direction.

However the tracking in the above-mentioned conventional configurations, involving manual regulation of the gain of the amplifier for the one-dimensional CCD prior to the tracking operation or of the gain of the image intensifier for adjusting the light amount entering the one-dimensional CCD, is cumbersome, requiring at least two operators. Besides it takes a long time, resulting in excessive light irradiation of the examinee. Also, the tracking utilizing automatic regulation of the gain of the amplifier for the one-dimensional CCD prior to the tracking operation or of the gain of the image intensifier for adjusting the light amount entering the one-dimensional CCD, is less cumbersome in operation, but such automatic regulation is also conducted even while the examiner looks for the target position to be tracked, so that the entire operation is similarly time-taking, resulting again in the excessive light irradiation of the examinee.

Also in such conventional configurations, since the electrical regulation of the amplifier gain or the regulation of the gain of the light amount entering the one-dimensional CCD from the image intensifier is conducted in such a manner that a non-vessel light region on the eye fundus is not saturated, the signal level for fine vessels of a low contrast becomes very small, hindering a satisfactory tracking operation.

Also in the actual measuring operation, the eye to be examined is not completely still but repeats fine movements even in the state of fixed gaze and the laser light has to follow such fine movements. However, in case of tracking a fine vessel with a low contrast which is positioned close to a large vessel with a high contrast, if the latter approaches to the center of tracking, for example, by the fine movement of the eyeball, the tracking may shift to the large vessel of the high contrast.

Furthermore, in the apparatus capable of tracking a moving object, there has not been disclosed a signal processing method for extracting the position of the vessel.

SUMMARY OF THE INVENTION

In consideration of the foregoing, a first object of the present invention is to provide an eye fundus blood flow meter that does not irradiate the eye fundus for an excessively long time, thereby reducing the burden to the eye to be examined.

A second object of the present invention is to provide an eye fundus blood flow meter which does not irradiate the photosensor means for an excessively long time, thereby enabling efficient use of the photosensor means for a prolonged period.

A third object of the present invention is to provide an ophthalmic apparatus not associated with the aforementioned drawbacks and capable of promptly and automatically regulating the gain of image taking means, thereby achieving measurement with minimum light irradiation.

A fourth object of the present invention is to provide an ophthalmic inspecting apparatus not associated with the aforementioned drawbacks and capable of exact and stable tracking operation for a desired eye fundus blood vessel.

BRIEF DESCRIPTION OF THE DRAWINGS

FIGS. 18A, 18B, 18C, 18D, 18E, 18F, 18G, 18H and 18I are timing charts showing a tracking signal;

FIGS. 20A, 20B, 20C, 20D, 20E, 20F, 20G, 20H and 20I are timing charts showing a tracking signal;

DETAILED DESCRIPTION OF THE PREFERRED EMBODIMENTS

At first there will be explained an eye fundus blood flow meter comprising irradiation means for irradiating the blood vessel on the eye fundus with laser light, photosensor means for receiving the laser light reflected by the eye fundus, and calculation means for starting a calculation for the optimum gain of the photosensor means in synchronization with the start of irradiation by the irradiation means.

Figure 1:
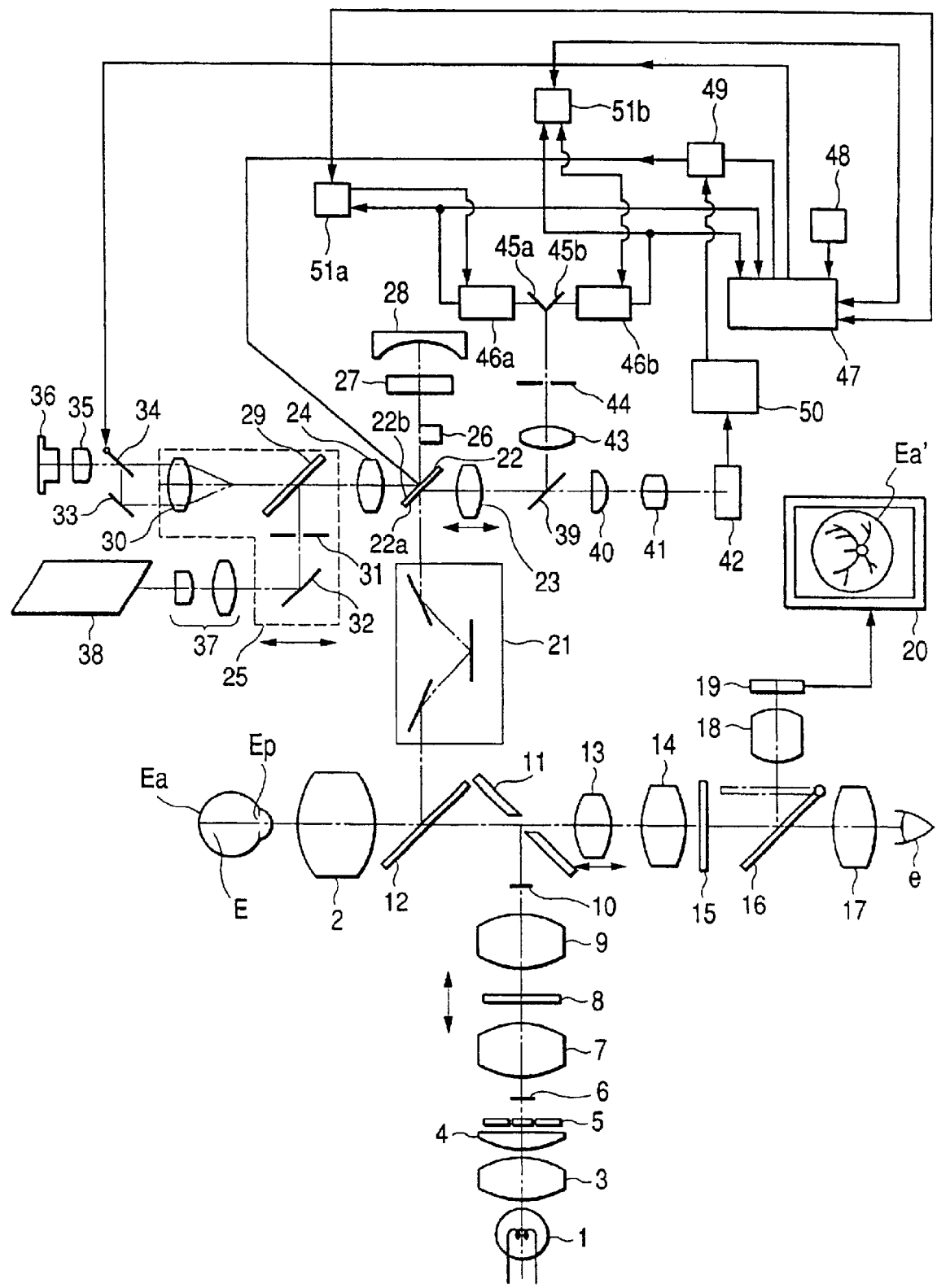
FIG. 1 is a view showing the configuration of an embodiment of the present invention.

FIG. 1 shows the configuration of an eye fundus blood flow meter constituting an embodiment of the present invention, in which, on an illumination optical path from an observation light source 1, composed for example of a tungsten lamp emitting white light, to an objective lens 2 opposed to an eye to be examined E, there are in succession provided a condenser lens 3, a field lens 4 with a band-pass filter transmitting, for example, only the yellow wavelength region, a ring slit 5 substantially conjugate with the pupil Ep of the eye to be examined E, a light shield member 6 substantially conjugate with the lens of the eye to be examined E, a relay lens 7, a transmissive liquid crystal plate 8 rendered movable along the optical path and serving as a fixed index display element, a relay lens 9, a light shield member 10 conjugate with the vicinity of the cornea of the eye to be examined E, a holed mirror 11, and a band-pass filter 12 transmitting the light of a yellow wavelength region and reflecting the light of other wavelength regions, thereby constituting an eye fundus illuminating optical system. The ring slit 5 and the light shield members 6, 10 serve to separate the eye fundus illuminating light and the eye fundus observing light at the front eye region of the eye to be examined E, and the shape of these components is not critical as long as a suitable light shielding area can be formed.

Behind the holed mirror 11 there is provided an eye fundus observing optical system, which is provided, in succession in the path to the observing eye e, a focusing lens 13 movable along the optical path, a relay lens 14, a scale plate 15, an optical path switching mirror 16 insertable into and retractable from the optical path, and an eyepiece lens 17. In an optical path in the direction of reflection of the optical path switching mirror 16 when it is inserted into the optical path, there are provided a television relay lens 18 and a CCD camera 19 whose output is supplied to a liquid crystal monitor 20.

Also in an optical path in the direction of reflection of the band-pass filter 12 there are provided an image rotator 21 and a galvanometric mirror 22 polished on both faces and having a rotary axis perpendicular to the plane of the drawing, and in the direction of reflection of the lower reflective face 22a of the galvanometric mirror 22 provided is a second focus lens 23 movable along the optical path, while, in the direction of reflection of the upper reflective face 22b, there are provided a lens 24 and a focusing unit 25. The front focal plane of the lens 24 is conjugate with the pupil Ep of the eye to be examined E and the galvanometric mirror 22 is positioned on such a focal plane.

Behind the galvanometric mirror 22 there are provided an optical path length compensating semi-circular plate 26, a black spot plate 27 having a light shield region in the optical path, and a concave mirror 28 in a concentric manner on the optical axis, thereby constituting a relay optical system for guiding the light beam, which is not reflected by the lower reflective face 22a of the galvanometric mirror 22, to the upper reflective face 22b thereof.

The optical path length compensating semicircular plate 25 is provided to compensate for the aberration, in the vertical direction of the drawing, resulting from the thickness of the galvanometric mirror 22 between the upper reflective face 22b and the lower reflective face 22a thereof, and functions only in the optical path toward the image rotator 21.

In the focusing unit 25 there are provided, on the same optical path of the lens 24, a dichroic mirror 29 and a condenser lens 30, and, on an optical path in the direction of reflection of the dichroic mirror 29 there are provided a mask 31 and a mirror 32. The focusing unit 25 is rendered integrally movable in a direction indicated by an arrow, along the optical path.

On an optical path at the entrance side of the condenser lens 30, there are provided a fixed mirror 33 and an optical path switching mirror 34 retractable from the optical path, and, on an optical path at the entrance side of the optical path switching mirror 34, there are provided a collimating lens 35 and a measuring laser diode 36 emitting coherent light, such as of a red color. Furthermore, on an optical path at the entrance side of the mirror 32 there are provided a beam expander 37 composed, for example, of a cylindrical lens, and a tracking light source 38 emitting light of a high intensity of a color, for example, green, different from that of the other light source.

On an optical path behind the second focusing lens 23, there are in succession provided a dichroic mirror 39, a field lens 40, a magnifying lens 41 and a one dimensional CCD 42 with an image intensifier, thereby constituting a vessel detection system. Also, on an optical path in the direction of reflection by the dichroic mirror 39, there are provided an imaging lens 43, a confocal diaphragm 44 and paired mirrors 45a, 45b substantially conjugate with the pupil Ep of the eye to be examined E, and, in the directions of reflection by the paired mirrors 45a, 45b there are respectively provided photomultipliers 46a, 46b to constitute measuring light receiving optical systems. All the optical paths are illustrated on the same plane for the purpose of simplicity, but the optical path from the laser diode 36 to the mask 31, the measuring optical path at the exit side of the tracking light source 38 and the reflection optical paths of the paired mirrors 45a, 45b are, in fact, perpendicular to the plane of the drawing.

For controlling the entire apparatus there is provided a system control unit 47, to which are supplied the outputs of the photomultipliers 46a, 46b and the output of input means 48 to be operated by the examiner. The output of the system control unit 47 is supplied to the optical path switching mirror 34 and a galvanometric mirror control circuit 49 for controlling the galvanometric mirror 22, and the galvanometric control circuit 49 receives the output of the one-dimensional CCD 42 through a vessel position detecting circuit 50. Also the outputs of the photomultipliers 46a, 46b are respectively supplied to optimum gain calculating portions 51a, 51b whose outputs are supplied to the system control unit 47.

Figure 2:
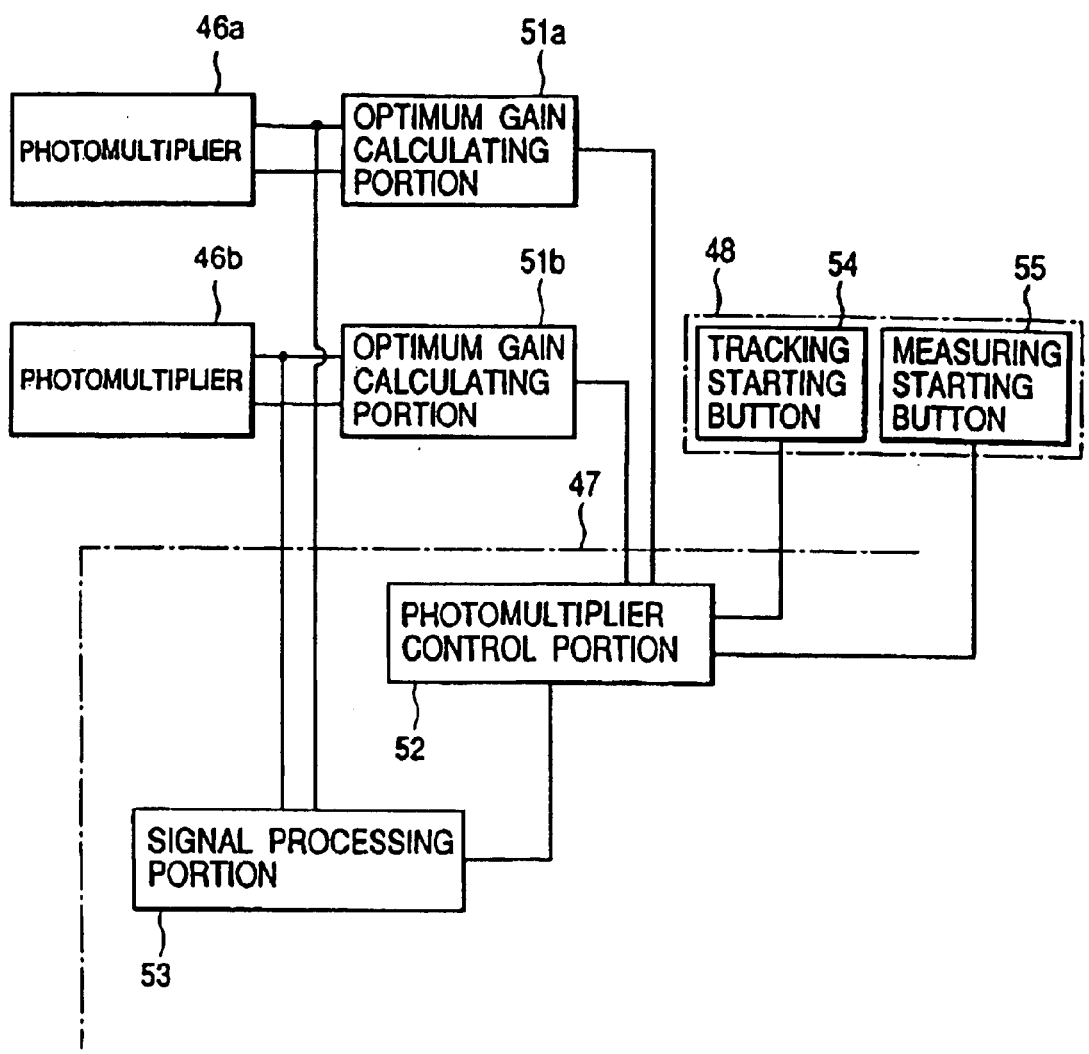
FIG. 2 is a view showing the configuration of a system control unit in the present invention.

FIG. 2 shows the internal configuration of the system control unit 47, which is provided therein with a photomultiplier control portion 52 and a signal processing portion 53. Other components will not be explained as they are not essential to the present invention. In the input means 48, the outputs of a tracking start button 54 and a measurement start button 55 are supplied to the photomultiplier control portion 52, whose outputs are supplied respectively to the photomultipliers 46a, 46b through the optimum gain calculating portions 51a, 51b. Also an output of the photomultiplier control portion 52 is supplied to the signal processing portion 53, whose outputs are supplied respectively to the photomultipliers 46a, 46b and the optical gain calculating portions 51a, 51b.

The white light emitted from the observing light source 1 is transmitted by the condenser lens 3. Then the light of the yellow wavelength region only is transmitted by the field lens 4 with the band-pass filter, is further transmitted by the ring slit 5, the light shield member 6 and the relay lens 7, illuminates the transmissive liquid crystal plate 8 from the rear side, is further transmitted by the relay lens 9 and the light shield member 10, and is reflected by the holed mirror 11. Thus, the light of the yellow wavelength region only is transmitted by the band-pass mirror 12 and the objective lens 2 and is focused as an eye fundus illuminating light beam on the pupil Ep of the eye to be examined E, thus uniformly illuminating the eye fundus Ea. In this state the transmissive liquid crystal plate 8 displays a fixation target which is projected by the illuminating light onto the eye fundus Ea of the eye to be examined E and is presented thereto as a target image.

The light reflected by the eye fundus Ea returns on the same optical path and is taken out, from the pupil Ep, as an eye fundus observing light beam, which is guided through the central hole of the holed mirror 11, the focusing lens 13, and the relay lens 14, is then focused as an eye fundus image Ea' by the scale plate 15 and reaches the optical path switching mirror 16. When the optical path switching mirror 16 is retracted from the optical path, the observing eye e can observe the eye fundus image Ea' through the eyepiece lens 17, but, when the optical path switching mirror 16 is inserted into the optical path, the eye fundus image Ea' focused on the scale plate 15 is refocused on the CCD camera 19 through the television relay lens 18 and is displayed on the liquid crystal monitor 20.

The alignment of the apparatus is made under the observation of the eye fundus image Ea' either through the eyepiece lens 17 or the liquid crystal monitor 20. In this operation it is desirable to select the appropriate observing method according to the desired purpose. The observation through the eyepiece lens 17, being generally higher in the resolving power and in the sensitivity than the observation by the liquid crystal monitor 20, is suitable for diagnosis by reading delicate changes on the eye fundus Ea. On the other hand, the observation through the liquid crystal monitor 20 is also very useful for clinical purposes since such observation, not limited in the viewing field, can reduce the fatigue of the examiner and allows electronic recording of the successive changes in the measured region of the eye fundus image Ea' by supplying the output of the CCD camera 19 to an external video cassette recorder or an external video printer.

The measuring light, emitted from the laser diode 36, is collimated by the collimating lens 35 and, if the optical path switching mirror 34 is inserted in the optical path, is reflected by this mirror 34 and the fixed mirror 33 to pass through the lower part of condenser lens 30, but, if the optical path switching mirror 34 is retracted from the optical path, it directly passes through the upper part of condenser lens 30, thus being transmitted by the dichroic mirror 29.

On the other hand, the tracking light emitted from the tracking light source 38 is expanded in beam diameter with different magnifications in the vertical and horizontal directions by the beam expander 37, then is reflected by the mirror 32, is shaped into a desired shape by the shaping mask 31, is further reflected by the dichroic mirror 29 and is superposed by the condenser lens 30 with the measuring light, which is focused into a spot at a position conjugate with the center of the aperture of the mask 31. The measuring light and the tracking light, mutually superposed, are transmitted by the lens 24, reflected by the upper reflective face 22b of the galvanometric mirror 22, transmitted by the black spot plate 27, reflected by the concave mirror 28, again transmitted by the black spot plate 27 and the optical path length correcting semicircular plate 26, and are returned toward the galvanometric mirror 22.

By the function of the relay optical system, which forms the image of the upper reflective face 22b and the lower reflective face 22a of the galvanometric mirror 22 with a magnification of −1, the measuring light and the tracking light reflected by the upper reflective face 22b are returned to the galvanometric mirror 22 in a state deviated from the optical axis of the objective lens 2, so that these lights are transmitted by the galvanometric mirror 22 without being reflected by the lower reflective face 22b thereof, further by the image rotator 21, then deflected by the band-pass filter 12 toward the objective lens 2 and projected therethrough to the eye fundus Ea of the eye to be examined E.

The light scattered and reflected at the eye fundus Ea is condensed by the objective lens 2, then is reflected by the band-pass filter 12, is transmitted by the image rotator 21, is reflected by the lower reflective face 22a of the galvanometric mirror 22, and is transmitted by the second focusing lens 23, and the measuring light and the tracking light are separated by the dichroic mirror 39.

The tracking light is transmitted by the dichroic mirror 39, and is focused by the field lens 40 and the imaging lens 41 on the one-dimensional CCD 42 as a vessel image which is magnified greater than the eye fundus image Ea' formed by the eye fundus observing optical system. Based on the vessel image taken by the one-dimensional CCD, the vessel position detection circuit 50 prepares data indicating the amount of displacement of the vessel image for supply to the control circuit 49, which drives the galvanometric mirror 22 so as to compensate for such an amount of displacement.

On the other hand, the measuring light is reflected by the dichroic mirror 39, is then transmitted by the aperture of the confocal diaphragm 44, is reflected in two directions by the paired mirrors 45a, 45b and received by the photomultipliers 46a, 46b, whose output signals are supplied to the system control unit 47 and are subjected to a frequency analysis to determine the blood flow velocity at the eye fundus Ea.

The outputs of the photomultipliers 46a, 46b are also supplied to the optimum gain calculating portions 51a, 51b for calculating the optimum gains, which are respectively fed back to the photomultipliers 46a, 46b.

When the tracking start button 54 of the input means 48 is depressed, the photomultiplier control portion 52 of the system control unit 47 sends a calculation start signal to the optimum gain calculating portions 51a, 51b, which in response, calculates the optimum gains of the photomultipliers 46a, 46b and sends these optimum gains to the photomultipliers 46a, 46b.

The optimum gain calculation portions 51a, 51b monitor whether the photomultipliers 46a, 46b are set at the optimum gains, and send gain setting signals to the photomultiplier control portion 52, which therefore can know whether the photomultipliers 46a, 46b are set at the optimum gains.

As the time required for setting the photomultipliers 46a, 46b at the optimum gains is in the order of several hundred milliseconds, such setting can be normally achieved within a time from the depression of the tracking start button 54 to the depression of the measurement start button 55.

Then, when the measurement start button 55 is depressed, the photomultiplier control portion 52 sends a calculation stop signal to the optimum gain calculating portions 51a, 51b and simultaneously sends a process start signal to the signal processing portion 53, whereby the optimum gain calculating portions 51a, 51b terminate the calculation, while the signal processing portion 53 executes a process for determining the blood flow velocity.

In case the setting of the photomultipliers 46a, 46b at the optimum gains cannot be completed within the time from the depression of the tracking start button 54 to the depression of the measurement start button 55, the measurement is started after such setting is completed.

The calculation of the optimum gain is terminated at the start of measurement, but it may be continued thereafter. Also, as the optimum gain calculating portions 51a, 51b are independently operable, the calculation may be terminated when each of the photomultipliers 46a, 46b reaches the optimum gain after the start of tracking. Also the calculation of the optimum gain is started at the start of tracking, but it may be started at the start of measurement.

When the tracking start button 54 of the input means 48 is depressed, a tracking start signal is supplied to the system control unit 47, which in response sends an optimum gain calculation start signal to the optimum gain calculating portions 51a, 51b and then monitors optimum gain setting completion signals therefrom. Confirming the reception of the optimum gain setting completion signals, the system control unit 47 sends a galvanometric mirror drive signal to the galvanometric mirror control circuit 49. Also, the vessel position detection circuit 50 prepares and outputs data, representing the amount of displacement of the vessel image, to the galvanometric mirror control circuit 49, which in response drives the galvanometric mirror 22 so as to compensate for the amount of displacement, whereby the vessel on the eye fundus Ea is tracked.

When the examiner depresses the measurement start button 55 of the input means 48 after confirming the state of tracking, the input means 48 sends a measurement start signal to the system control unit 47, which determines the blood flow velocity by analyzing the Doppler signals from the photomultipliers 46a, 46b. In this state, the gains of the Doppler signals therefrom, tracking the same vessel, are adjusted to the optimum gains.

Also in case of measuring the blood flow velocity of the vessel of a different position of the same person or the blood flow velocity of the vessel of a different person, the measurement can be executed by determining the vessel to be measured and setting the optimum gains at the start of tracking in a similar manner. Consequently, the examiner can execute the measurement without paying attention to whether the photomultipliers 46a, 46b are set at the optimum gains, and the loads on and deterioration of the photomultipliers 46a, 46b can therefore be reduced, in comparison with the case where the optimum gains for the photomultipliers 46a, 46b are constantly determined. Also, the operation by the examiner for determining the optimum gains for the photomultipliers 46a, 46b causes an additional light irradiation of the eye to be examined E, but the present embodiment can reduce the damage to the eye to be examined E.

Figure 3:
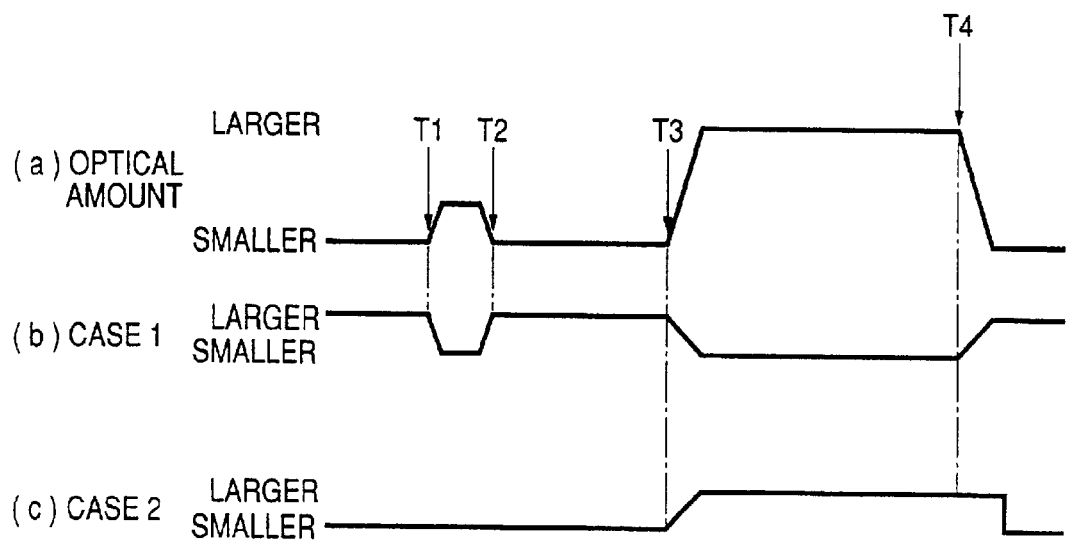
FIGS. 3 and 4 are timing charts showing an optimum gain setting operation of the present invention.

FIG. 3 is a timing chart, in which (a) indicates the incident light amount on the photomultipliers 46a, 46b, and which compares a case 1 (b) of constantly setting the optimum gains for the photomultipliers 46a, 46b and a case 2 (c) of setting the optimum gains at the start of the tracking operation as in the present embodiment.

In a period T1–T2, if light other than the Doppler shift light enters the photomultipliers 46a, 46b, the gain varies so as to attain an optimum gain in the case 1 in which the optimum gain is constantly determined, but the gain does not change in the case 2 in which the optimum gain is determined prior to the start of the tracking operation. Consequently, case 1 executes the gain setting more frequently than in case 2, whereby the loads to the photomultipliers 46a, 46b increase. Also, in case 1, the gain is set at a maximum immediately before the start of the tracking operation at T3 because the light amount is very weak, and the photomultipliers 46a, 46b receive a large amount of light in a stage of maximum gain at T3, and this is undesirable for the photomultipliers 46a, 46b. On the other hand, in the case 2, the gain is set at a minimum at the end T4 of the measurement and is maintained at this level until the tracking operation is started at T3.

Consequently, the present embodiment allows use of the photomultipliers 46a, 46b in an efficient manner, over a prolonged period.

Figure 4:
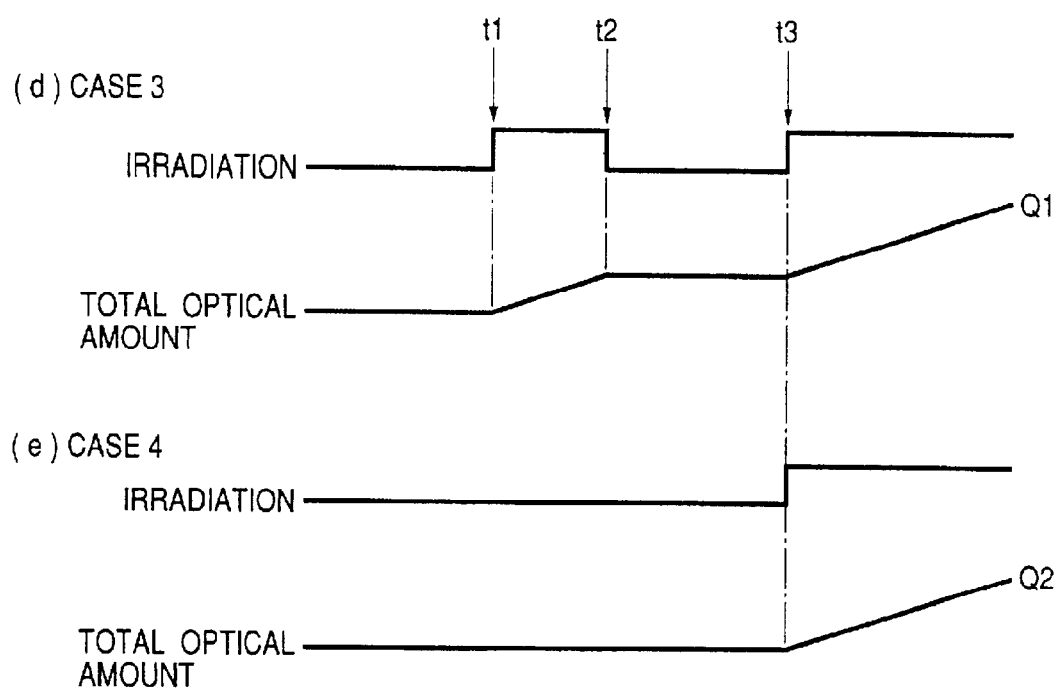

FIG. 4 is a timing chart comparing a case 3 (d) in which the optimum gains for the photomultipliers 46a, 46b are set by the examiner, and a case 4 (e) in which the optimum gains are automatically determined. The chart shows the timing of entry of the measuring light into the eye to be examined E, and the total light amount Q1 or Q2 indicates the total sum of the light amount entering into the eye to be examined E.

In the case 3 in which the examiner sets the optimum gains, the examiner sets the optimum gains for the photomultipliers 46a, 46b under the same conditions as in the measurement in the period from T1 to T2, so that the measuring light enters the eye to be examined E during this period. On the other hand, in the case 4 in which the optimum gains are determined at the start of tracking, the examiner is not required to set the optimum gains for the photomultipliers 46a, 46b under the same conditions as in the measurement in the period from T1 to T2, and the optimum gains are set simultaneously with the start of tracking at T3. Consequently, in comparison with the foregoing case 3, the eye to be examined E can be prevented from the entry of the measuring light in the unnecessary period.

Therefore, the present embodiment does not irradiate the eye to be examined E with the measuring light in the unnecessary period, thereby reducing the burden on the eye to be examined E.

As explained in the foregoing, the eye fundus blood flow meter of the present invention can determine the optimum gains of the light receiving means immediately before the measuring operation, by starting the calculation of the optimum gain in synchronization with the start of irradiation, thereby exactly determining the blood flow velocity in the eye fundus Ea and reducing the light irradiating time to the eye to be examined.

Also, since the eye fundus blood flow meter of the present invention starts the calculation of the optimum gains in synchronization with the start of tracking, it need not execute the gain calculation for the light receiving means in a continuous manner, thereby reducing the damage thereto.

In the following, there will be explained an apparatus comprising illumination means for illuminating an eye fundus area including a specified target region; detection means for detecting the light from such specified region; tracking means for executing a tracking operation following the movement of the eye fundus, utilizing the detection signal of the detection means; tracking start input means for outputting an input signal for starting the tracking of the tracking means; amplification gain determination means for determining the amplification gain of the detection means, based on an output signal therefrom; and control means for executing, in succession, a first step for causing the amplification gain determination means to determine the amplification gain of the detection means in response to the input signal from the tracking start input means and a second step for causing the tracking means to start the tracking with the amplification gain determined by the first step.

Figure 5:
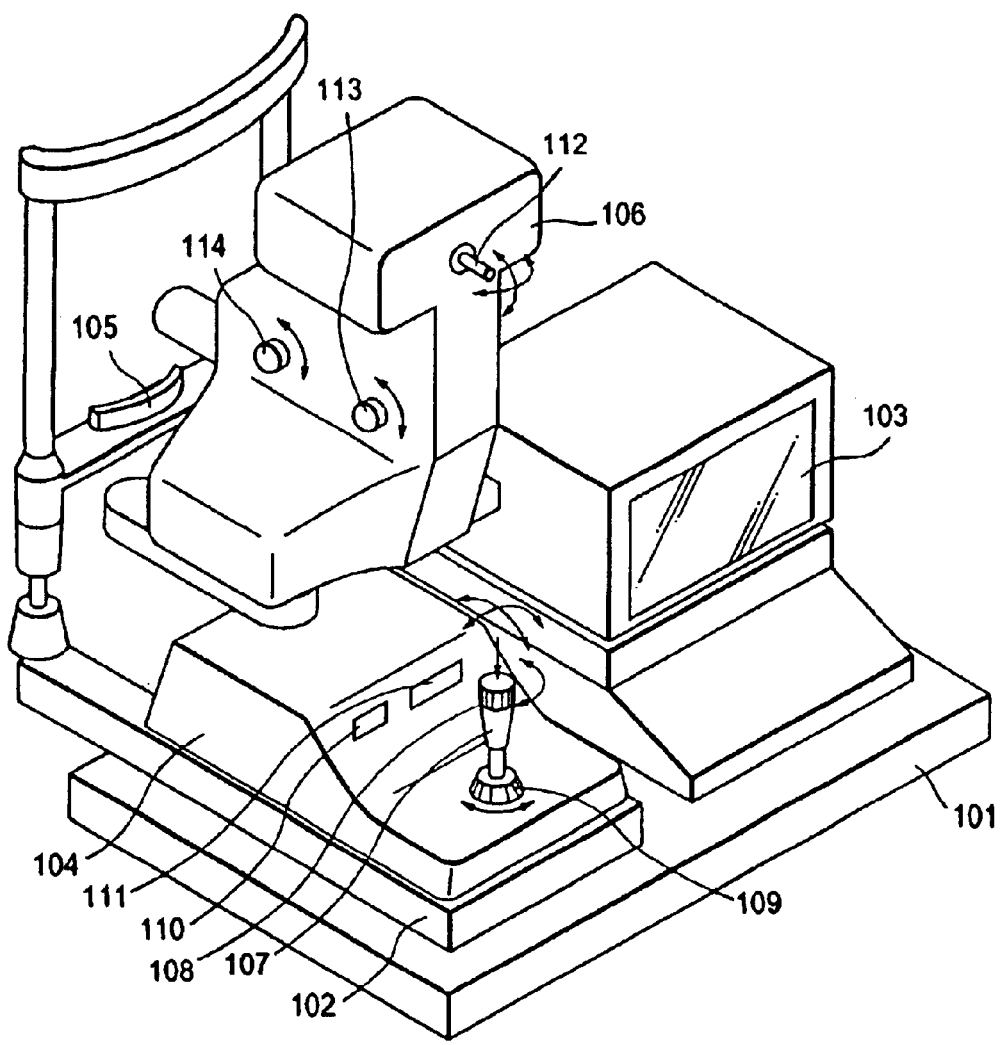
FIG. 5 is a perspective view of an embodiment of the present invention.

FIG. 5 is a perspective view of the eye fundus blood flow meter of the present embodiment, wherein a base member 101 supports a monitor 103 and a fixed stage unit 102, which in turn, supports a movable stage unit 104 rendered movable in the forward-backward direction and in the lateral direction, and a chin support member 105. On the movable stage unit 104 there is provided a measuring head 106, and, at the examiner side of the movable stage 104 there are provided an operating rod 107, a switch 108, an operation ring 109, a measuring mode selecting switch 110 and an LED 111 for display. Also on the measuring head 106 there are provided an operation knob 112 for moving a fixation target, a focusing knob 113, and an image rotator knob 114.

Figure 6:
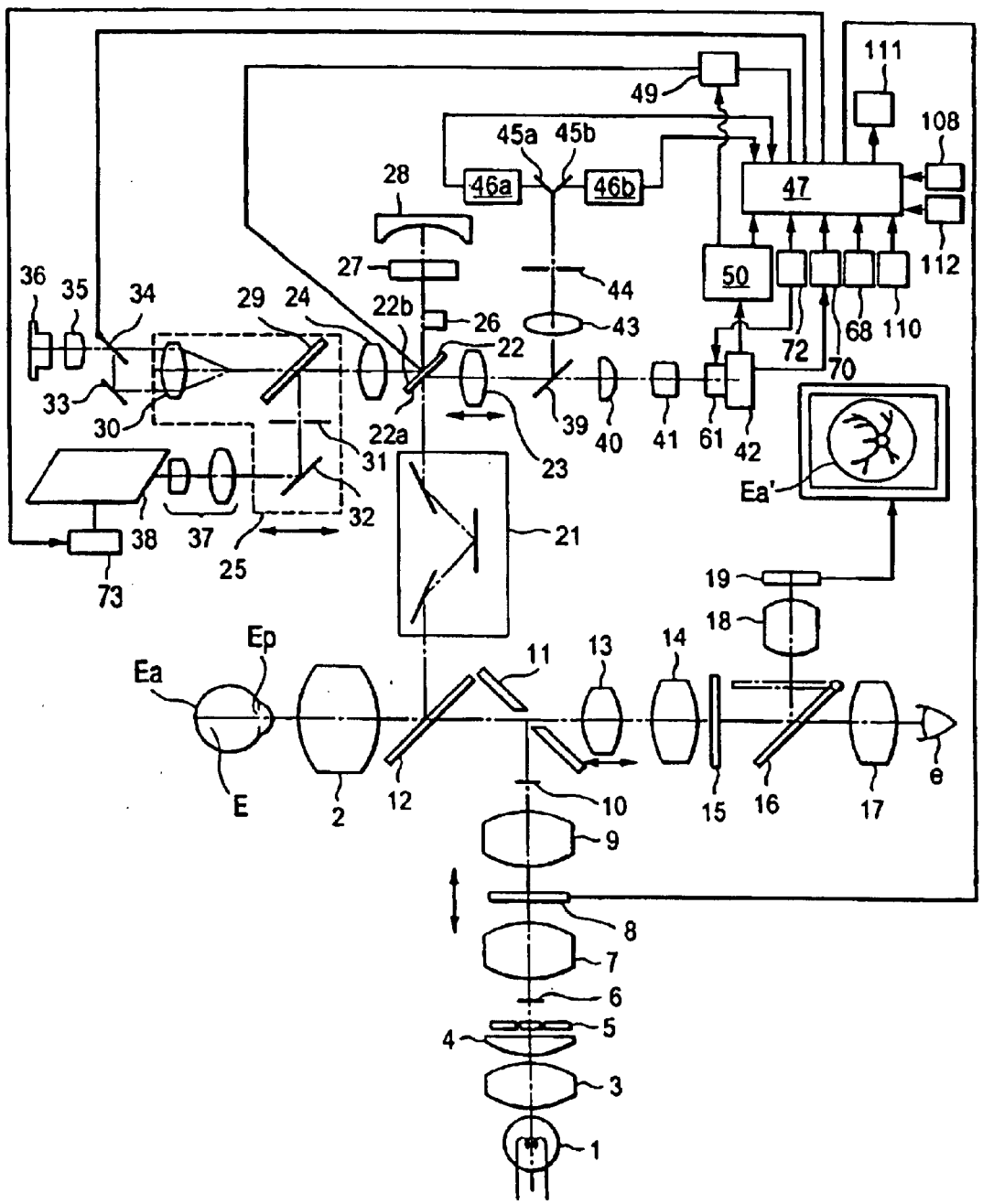
FIG. 6 is a view showing the configuration of a measuring head of the present invention.

FIG. 6 is a view showing the configuration of a main body of the eye fundus blood flow meter, incorporated in the measuring head 106, wherein, on an illumination optical path from an observation light source 1 composed for example of a tungsten lamp emitting white light to an objective lens 2 provided in a position opposed to the eye to be examined E, there are in succession provided a condenser lens 3, a field lens 4 with a band-pass filter for transmitting, for example, light of the yellow wavelength region only, a ring slit 5 substantially conjugate with the pupil Ep of the eye to be examined E, a light shield member 6 substantially conjugate with the lens of the eye to be examined E, a relay lens 7, a transmissive liquid crystal panel 8 rendered movable along the optical path and constituting a fixation target displaying element, a relay lens 9, a light shield member 10 conjugate with the vicinity of the cornea of the eye to be examined E, a holed mirror 11, and a band-pass mirror 12 transmitting light of the yellow wavelength region and substantially reflecting light of other wavelength regions, thereby constituting an illumination optical system.

The ring slit 5 and the light shield members 6, 10 serve to separate the eye fundus illuminating light and the eye fundus observing light at the front eye region of the eye to be examined E, and the shape of these components is not critical as long as a suitable light shielding area can be formed.

Behind the holed mirror 11 there is provided an eye fundus observing optical system, which is provided, in succession on the path to the observing eye e, a focusing lens 13 moveable along the optical path, a relay lens 14, a scale plate 15, an optical path switching mirror 16 insertable into and retractable from the optical path, and an eyepiece lens 17. In an optical path in the direction of reflection of the optical path switching mirror 16 when it is inserted into the optical path, there are provided a television relay lens 18 and a CCD camera 19 whose output is supplied to a CRT monitor 103.

Also in an optical path in the direction of reflection of the band-pass filter 12, there are provided an image rotator 21 and a galvanometric mirror 22 polished on both faces and having a rotary axis perpendicular to the plane of the drawing, and in the direction of reflection of the lower reflective face 22a of the galvanometric mirror 22 provided is a second focusing lens 23 movable along the optical path, while, in the direction of reflection of the upper reflective face 22b, there are provided a lens 24 and a focusing unit 25. The front focal plane of the lens 24 is conjugate with the pupil Ep of the eye to be examined E and the galvanometric mirror 22 is positioned on such focal plane.

Above the galvanometric mirror 22 there are provided an optical path length compensating semi-circular plate 26, a black spot plate 27 having a light shield portion in the optical path, and a concave mirror 28 positioned in a concentric manner on the optical axis, thereby constituting a relay optical system for guiding the light beam, which is not reflected by the lower reflective face 22a of the galvanometric mirror 22, to the upper reflective face 22b thereof.

The optical path length compensating semicircular plate 26 is designed to compensate for the aberration, in the vertical direction of the drawing, resulting from the thickness of the galvanometric mirror between the upper reflective face 22b and the lower reflective face 22a thereof, and functions only in the optical path toward the image rotator 21.

In the focusing unit 25 there are provided, on the optical path of the lens 24, a dichroic mirror 29 and a condenser lens 30, and, on an optical path in the direction of reflection of the dichroic mirror 29, there are provided a mask 31 and a mirror 32. The focusing unit 25 is rendered integrally movable in a direction indicated by an arrow, along the optical path.

On an optical path at the entrance side of the condenser lens 30, there are provided in a parallel manner a fixed mirror 33 and an optical path switching mirror 34 retractable from the optical path, and, on an optical path at the entrance side of the optical path switching mirror 34, there are provided a collimating lens 35 and a measuring laser diode 36 emitting coherent light, such as light of a red color. Furthermore, on an optical path at the entrance side of the mirror 32 there are provided a beam expander 37 composed, for example, of a cylindrical lens, and a tracking light source 38 emitting light of a high intensity of a color, for example, green, different from that of the other light source.

On an optical path behind the second focusing lens 23, there are in succession provided a dichroic mirror 39, a field lens 40, a magnifying lens 41 and a one dimensional CCD 42 with an image intensifier, thereby constituting a vessel detection system. Also, on an optical path in the direction of reflection by the dichroic mirror 39, there are provided an imaging lens 43, a confocal diaphragm 44 and paired mirrors 45a, 45b substantially conjugate with the pupil Ep of the eye to be examined E, and, in the directions of reflection by the paired mirrors 45a, 45b there are respectively provided photomultipliers 46a, 46b to constitute measuring light receiving optical systems. All the optical paths are illustrated on a same plane for the purpose of simplicity, but the optical path from the laser diode 36 to the mask 31, the measuring optical path at the exit side of the tracking light source 38 and the reflection optical paths of the paired mirrors 45a, 45b are, in fact, perpendicular to the plane of the drawing.

For controlling the entire apparatus there is provided a system control unit 47, to which are supplied the outputs of the switch 108, the measuring mode selection switch 110, the operation knob 112, the photomultipliers 46a, 46b and lateral movement detection means 68. The output of the one-dimensional CCD 42 is supplied through a vessel detection circuit 50 and an A/D converter 70 to the system control unit 47, while the output of the vessel detection circuit 50 is supplied to the system control unit 47 and to a galvanometric mirror control circuit 49 for controlling the galvanometric mirror 22, and the output of the system control unit 47 is supplied, through the display LED 111, the transmissive liquid crystal plate 8, the optical path switching mirror 34, the galvanometric mirror control circuit 49 and a D/A converter 72, to a driving power source 73 for the tracking light source 38 and the image intensifier 61.

Figure 7:
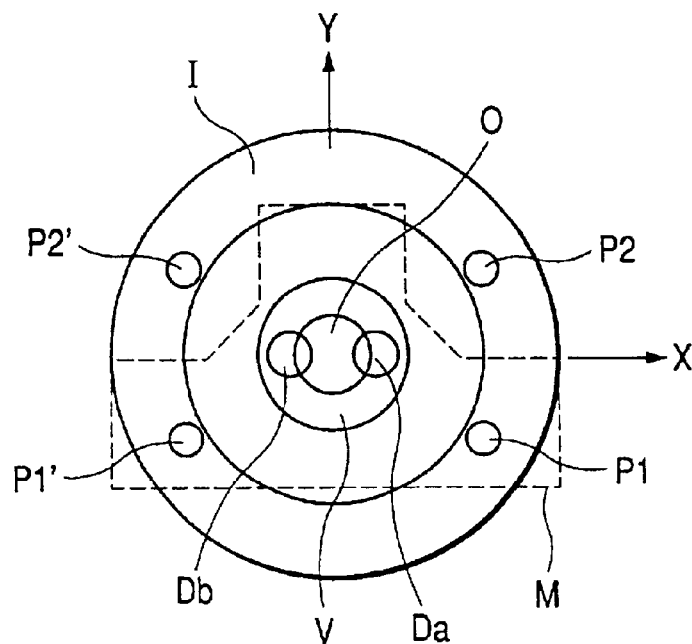
FIG. 7 is a view showing the arrangement of light beams on the pupil, in the present invention.

FIG. 7 shows the arrangement of light beams on the pupil Ep of the eye to be examined E, wherein I indicates an area illuminated with the yellow illuminating light and shows an image of the ring slit 5, O indicates an eye fundus observing light beam and shows an image of the aperture of the holed mirror 11, V indicates a measuring light beam/beam received from the vessel and shows an image of effective portions of the upper and lower reflective faces 22b, 22a of the galvanometric mirror 22, and Da, Db indicate two received measuring beams and respectively show images of the paired mirrors 45a, 45b. Also P1, P1' indicate the entering positions of the measuring light selected by the switching of the optical path switching mirror 34, and a chain-lined area M indicates an image of the lower reflective face 22a of the galvanometric mirror 22.

At the measurement, the examiner at first fixes the face of the examinee on the chin support member 105, and selects, for example, a mode for measuring a vessel in the vicinity of the disc by the measuring mode selecting switch 110. The lateral position of the movable stage 104 is detected by the lateral movement detection means 68 to discriminate whether the eye to be examined is the left or right eye, and the signals from the lateral movement detection means 68 and the measuring mode selecting switch 110 are supplied to the system control unit 47. In response to these signals, a predetermined dot pattern Q is displayed as the fixation target on the transmissive liquid crystal plate 8, and the observation light source 1 is turned on.

The white light emitted from the observing light source 1 is transmitted by the condenser lens 3. Then, the light of the yellow wavelength region only is transmitted by the field lens 4 with the band-pass filter, is further transmitted by the ring slit 5, the light shield member 6 and the relay lens 7, illuminates the transmissive liquid crystal plate 8 from the rear side, is further transmitted by the relay lens 9 and the light shield member 10, and is reflected by the holed mirror 1. Thus the light of the yellow wavelength region only is transmitted by the band-pass mirror 12 and the objective lens 2 and is focused as an image I of the eye fundus illuminating light beam on the pupil Ep of the eye to be examined E, thus substantially uniformly illuminating the eye fundus Ea.

In this state, the transmissive liquid crystal plate 8 displays one of the dot patterns Q, which is projected by the illuminating light onto the eye fundus Ea of the eye to be examined E and is presented thereto as an fixation target image F. The examiner manipulates the operating knob 112 to send a signal to the system control unit 47, thereby varying the position of the displayed dot pattern Q and guiding the visual axis of the eye to be examined E.

The light reflected by the eye fundus Ea returns on the same optical path and is taken out, from the pupil Ep, as an eye fundus observing light beam O, which is guided through the central hole of the holed mirror 11, the focusing lens 13, and the relay lens 14, is then focused as an eye fundus image Ea' by the scale plate 15 and reaches the optical path switching mirror 16. When the optical path switching mirror 16 is retracted from the optical path, the observing eye e can observe the eye fundus image Ea' through the eyepiece lens 17, but, when the optical path switching mirror 16 is inserted into the optical path, the eye fundus image Ea' focused on the scale plate 15 is refocused on the CCD camera 19 through the television relay lens 18 and is displayed on the monitor 103.

The alignment of the apparatus with the eye to be examined E is made by the manipulation of the operating rod 107 and the operating ring 109 to move the movable stage 104 in the X-Z plane and in the Y-direction, under the observation of the eye fundus image Ea' either through the eyepiece lens 17 or the monitor 103. In this operation it is desirable to select the appropriate observing method according to the desired purpose. The observation through the eyepiece lens 17, being generally higher in resolving power and in sensitivity than the observation by the monitor 103, is suitable for diagnosis by reading delicate changes on the eye fundus Ea. On the other hand, observation through the monitor 103 is also very useful for clinical purposes since such observation, not limited in the viewing field, can reduce the fatigue of the examiner and allows electronic recording of the successive changes in the measured region of the eye fundus image Ea' by supplying the output of the CCD camera 19 to an external video cassette recorder or an external video printer.

Then, the measuring laser diode 36 and the tracking light source 38 are turned on. The measuring light, emitted from the laser diode 36, is collimated by the collimating lens 35 and, if the optical path switching mirror 34 is inserted in the optical path, is reflected by this mirror 34 and the fixed mirror 33 to pass through the lower part of condenser lens 30, but, if the optical path switching mirror 34 is retracted from the optical path, it directly passes through the upper part of condenser lens 30, thus being transmitted by the dichroic mirror 29.

On the other hand, the tracking light emitted from the tracking light source 38 is expanded in beam diameter with different magnifications in the vertical and horizontal directions by the beam expander 37, then is reflected by the mirror 32, is shaped into a desired shape by the shaping mask 31, is further reflected by the dichroic mirror 29 and is superposed by the condenser lens 30 with the measuring light which is focused into a spot at a position conjugate with the center of the aperture of the mask 31.

The measuring light and the tracking light, which are mutually superposed are transmitted by the lens 24, reflected by the upper reflective face 22b of the galvanometric mirror 22, transmitted by the, black spot plate 27, reflected by the concave mirror 28, again transmitted by the black spot plate 27 and the optical path length correcting semicircular plate 26, and are returned toward the galvanometric mirror 22.

By the function of the relay optical system, which consists of the concave mirror 28, the black spot plate 27 and the optical path length compensating semicircular plate 26, and which forms the images of the upper reflective face 22b and the lower reflective case 22a of the galvanometric mirror 22 with a magnification of −1, the measuring light and the tracking light reflected at positions P1, P1' shown in FIG. 3, behind the image M of the galvanometric mirror 22, are returned, by the insertion or retraction of the optical path switching mirror 34 into or from the optical path, to positions P2, P2' corresponding to a notched portion of the galvanometric mirror 22, so that these lights are guided to the image rotator 21 without being reflected by the galvanometric mirror 22. Then, the both light beams are deflected by the band-pass filter 12 toward the objective lens 2 and are projected therethrough to the eye fundus Ea of the eye to be examined E.

In this manner, the measuring light and the tracking light are reflected by the upper reflective face 22b of the galvanometric mirror 22, and, in the returning state, they enter the galvanometric mirror 22 in a state deviated from the optical axis of the objective lens 2, whereby, on the pupil Ep, the light beam passing through the positions P1 and P2 forms a spot image P, while the light beam passing through the positions P1' and P2' forms a spot image P', thereby illuminating the eye fundus Ea in spot shapes.

The light scattered and reflected at the eye fundus Ea is condensed by the objective lens 2, is then reflected by the band-pass filter 12, transmitted by the image rotator 21 and reflected by the lower reflective face 22a of the galvanometric mirror 22, and the measuring light and the tracking light are separated by the dichroic mirror 39.

The tracking light is transmitted by the dichroic mirror 39, and is focused by the field lens 40 and the imaging lens 41 on the one-dimensional CCD 42 through the image intensifier 61 as a vessel image Ev', which is magnified to a greater extent than the eye fundus image Ea' formed by the eye fundus observing optical system. On the other hand, the measuring light is reflected by the dichroic mirror 39, is then transmitted by the aperture of the confocal diaphragm 44, reflected in two directions by the paired mirrors 45a, 45b and received by the photomultipliers 46a, 46b.

In this state, because of the spectral characteristics of the band-pass mirror 12, the illuminating light from the observing light source 1 does not reach the one-dimensional CCD 42, and undesirable flare is reduced because a narrow image taking area is selected. As a result, the one-dimensional CCD 42 only takes the vessel image Ev' formed by the tracking light. Also, since hemoglobin in the blood and melamine in the pigment epithelium are significantly different in spectral reflectance in the green wavelength region, the vessel image Ev' can be obtained with a satisfactory contrast by employing green tracking light.

The light beam received by the one-dimensional CCD 42 is taken out from the measuring/vessel-received light beam V from the vessel at the pupil Ep of the eye to be examined E, and measuring/received light beams Da, Db are taken out therefrom by the paired mirrors 45a, 45b and are received by the photomultipliers 46a, 46b. The measuring/vessel-received light beam V is made larger than the eye fundus observing light beam O because otherwise a sufficient image plane intensity on the one-dimensional CCD 42 cannot be obtained as the one-dimensional CCD 42 has a larger imaging magnification for the eye fundus Ea than in the CCD camera 19 of the eye fundus observing optical system. On the other hand, the influence of flare, generated at the front eye region of the eye to be examined E by the enlargement of the light beam is negligible because the image receiving area is smaller in the vessel image receiving optical system. Also, the distance of the received measuring light beams Da, Db on the pupil E, directly affecting the resolving power of the blood flow velocity measurement, can be made sufficiently large by employing a large measuring/received light beam V.

Figure 8:
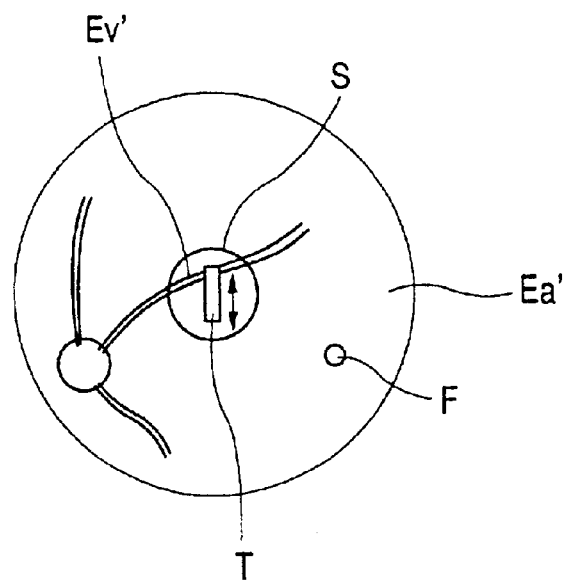
FIG. 8 is a schematic view showing an eye fundus image in the present invention.

A part of the measuring and tracking lights scattered and reflected on the eye fundus Ea is transmitted by the band-pass mirror 12 and guided to the eye fundus observing optical system positioned behind the holed mirror 11, wherein the tracking light is focused on the scale plate 15 as a rod-shaped indicator T, while the measuring light is focused as a spot at the center of the indicator T. FIG. 8 shows the eye fundus image Ea' observed through the eyepiece lens 17 or the monitor 103, including a vessel image Ev', an image F of the fixation target projected by the illuminating light onto the eye fundus, an indicator T superposed with an unrepresented spot image, and a circular scale S formed on the scale plate 15 and projected onto the eye fundus Ea. Under the observation of such an image, the examiner can one dimensionally move the indicator T within a range that the center of the indicator T is contained in the scale S, by the rotation of the switch 108.

When the examiner rotates the focusing knob 113 for focusing the eye fundus image Ea', the transmissive liquid crystal panel 8, the focusing lenses 13, 23 and the focusing unit 25 are moved in mutual linkage, by unrepresented drive means, along the optical axis. When the eye fundus image Ea' is focused, all the transmissive liquid crystal panel 8, the scale plate 15, the one-dimensional CCD 42, and the confocal diaphragm 44 become conjugate with the eye fundus Ea.

After the focusing operation, the examiner manipulates the operating knob 112, if necessary, to move the fixation target F, thereby guiding the visual axis of the eye to be examined E, thus varying the observed area and moving the target vessel Ev into the circle S of the scale plate 15. Then, the examiner drives the image rotator 21 by the image rotator knob 114, thereby rotating the indicator T in such a manner that it becomes perpendicular to the longitudinal direction of the target vessel Ev.

In this operation, the examiner recognizes whether the indicator T alone rotates, since the eye fundus observing light does not pass through the image rotator 21. Consequently also the images of the optical components on the pupil Ep as shown in FIG. 7 rotate in the same direction and by the same angle about the original point, so that a line passing through the centers of the measuring/received light beams Da, Db and the X-axis passing through the centers of the spot images P, P' become parallel to the longitudinal direction of the vessel Ev. As the blood flow velocity is determined from the interference between the scattered/reflected light from the vessel wall and that from the blood cells in the blood, the result of measurement is not influenced by the movement of the eye fundus Ea in the X-direction in the course of measurement, if the vessel Ea is positioned substantially parallel to the X-axis.

On the other hand, in case the eye fundus Ea moves in a direction of the Y-axis, which is perpendicular to the X-axis, the result of measurement becomes unstable because the light beam from the measuring laser diode 36 becomes deviated from the target vessel Ev, but, in such case, the amount of displacement of the vessel Ev need only be detected in the Y-direction. In the present embodiment, the tracking operation is executed only in such direction by the vessel detecting system behind the dichroic mirror 39 and by the galvanometric mirror 22.

Figure 9:
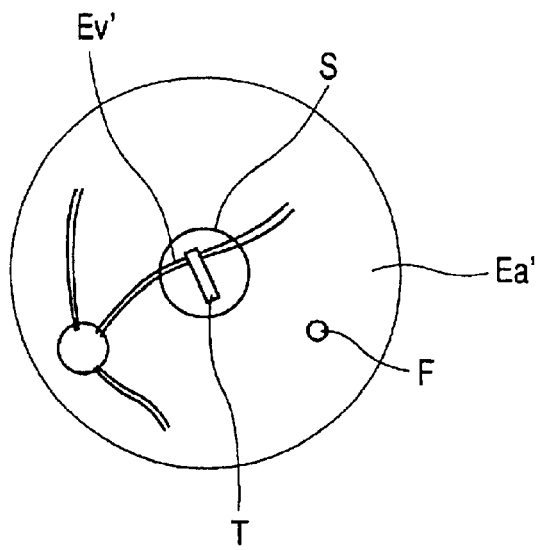
FIG. 9 is a schematic view showing a rotation of an indicator according to the present invention.
Figure 10:
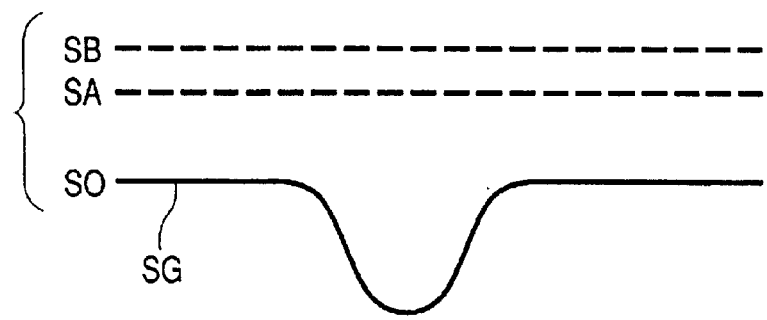
FIG. 10 is a chart showing the signal of the one dimensional CCD prior to the gain control, in the present invention.

As the elements of the one-dimensional, CCD 42 are arranged in the longitudinal direction of the tracking light, in a state where the angular adjustment of the inspected region is completed as shown in FIG. 9, the longitudinal direction of the indicator T, indicating the tracking light, is perpendicular to the longitudinal direction of the inspected vessel Ev, whereby the one-dimensional CCD 42 of the vessel detecting system takes the eye fundus image Ea indicated by the indicator T in a magnified manner. As the green tracking light is absorbed by the blood vessel, the output signal SG of the one-dimensional CCD 42 shows a recess, as shown in FIG. 10, at the crossing portion of the indicator T and the vessel Ev.

Figure 11:
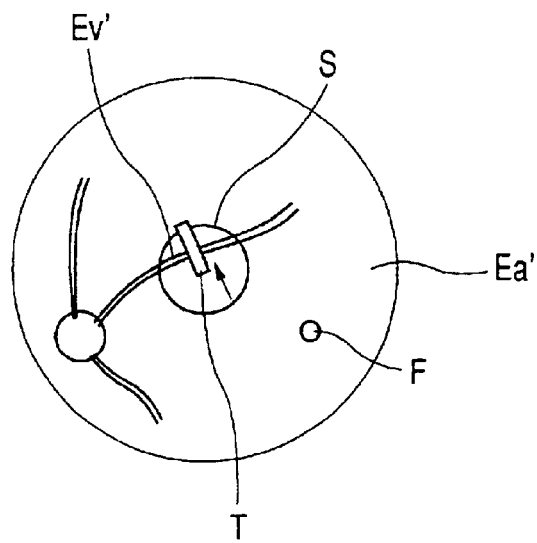
FIG. 11 is a schematic view showing a movement of the indicator in the present invention.

After the angular adjustment, the switch 108 is again rotated to move the indicator T as indicated by an arrow in FIG. 11, and the region to be measured is selected by matching the light spot, superposed with the tracking light, with such region. After the determination of the region to be measured, the switch 108 is pressed in to send a signal for starting the tracking operation after the positioning operation.

Figure 12:
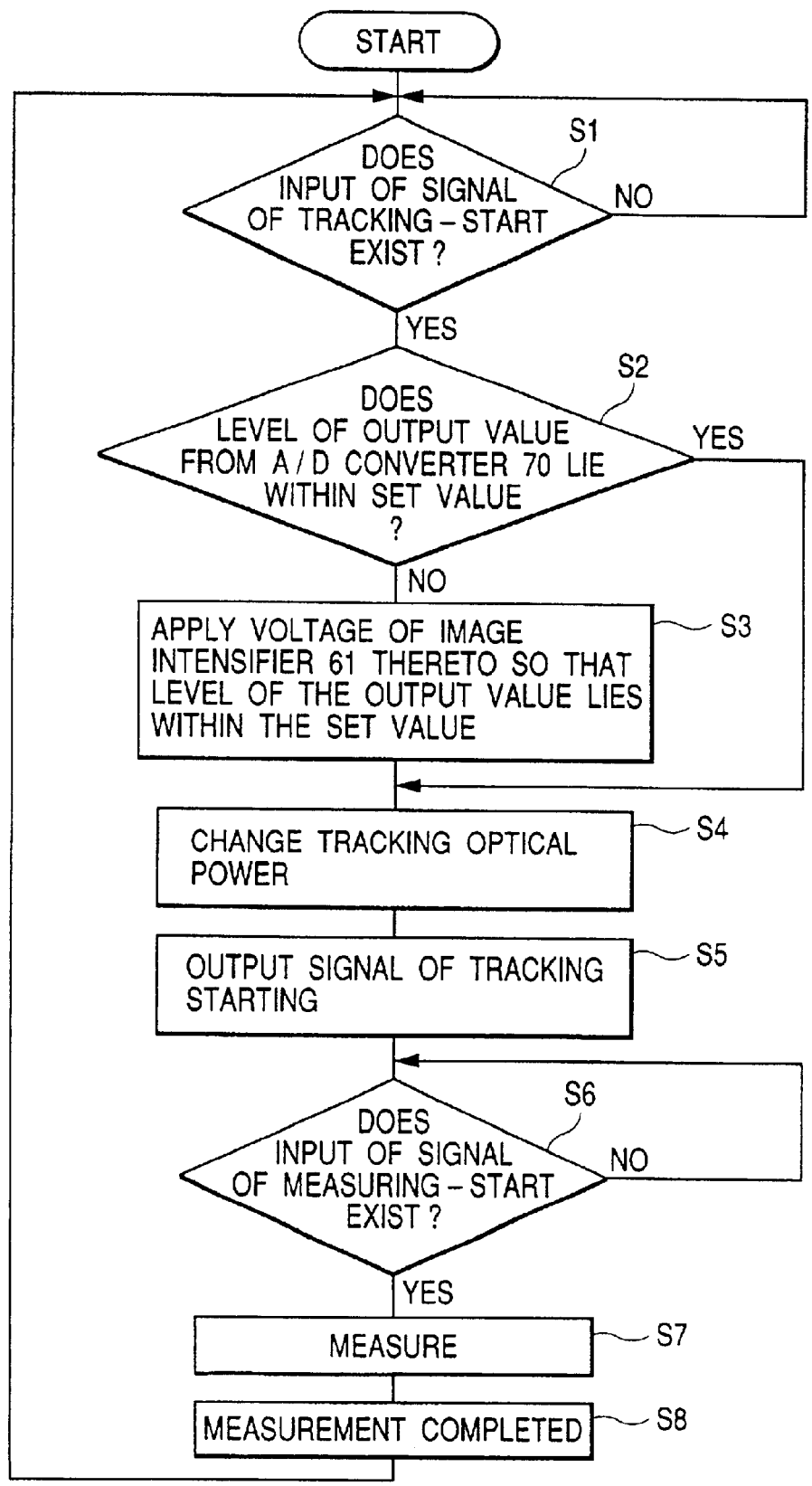
FIG. 12 is a flow chart showing the control sequence of the system control unit of the present invention.

In response to the tracking start signal entered from the switch 108, the system control unit 47 functions according to the flow chart shown in FIG. 12. A step S1 discriminates whether a tracking start signal has been entered from the switch 108, and, if entered, a step S2 executes A/D conversion of the signal SG from the one-dimensional CCD 42, shown in FIG. 10, by the A/D converter 70. Then, there is discriminated whether the signal SG is positioned within a range between values SA and SB which are shown in FIG. 10 and are present with such an initial power that is anticipated to bring the signal SG, coming from an area outside the vessel, to a preferred level in case the power of the tracking light irradiating the eye to be examined E is increased. If the signal SG is not within such range, a step S3 determines the voltage to be applied to the image intensifier 61 in such a manner that the signal SG falls between the set values SA and SB, and sends necessary data to the D/A converter 72 to execute such voltage application. In the present embodiment, the signal level of the vessel image Ev' is optimized by the control of the voltage applied to the image intensifier, but there may be controlled the gain of the amplifier of the one-dimensional CCD 42 for the same purpose.

Figure 13:
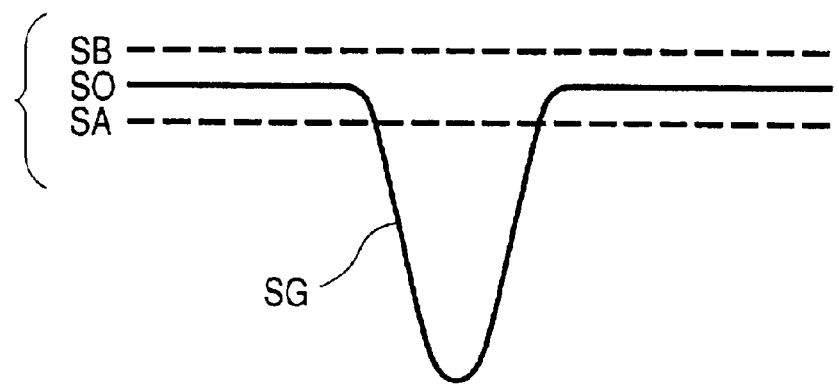
FIG. 13 is a chart showing the signal of the one dimensional CCD after to the gain control, in the present invention.

If the signal SG from an area outside the vessel is positioned between the set values SA and SB as shown in FIG. 13 from the beginning or after the step S3, the voltage applied to the image intensifier 61 is fixed, and, in a step S4, the system control unit 47 supplies the driving power source 73 with an instruction to increase the power of the tracking light to a preset power level required for ensuring the tracking operation.

Then, in a step S5, the system control unit 47 supplies the galvanometric mirror control circuit 49 with a tracking start signal, and the vessel detection circuit 49 calculates, based on the output signal of the one-dimensional CCD 42, the amount of the displacement of the vessel image Ev' from a one-dimensional reference position. Based on such amount of displacement, the galvanometric mirror control circuit 49 drives the galvanometric mirror 22 in such a manner that the position of the vessel image Ev' remains constant on the one-dimensional CCD 42.

After confirming the start of tracking, the examiner presses in the switch 108 further to initiate the measurement by a second-stroke switch. The system control unit 47 awaits, in a step S6 of the flow chart in FIG. 12, the entry of the measurement start signal from the switch 108, and, in response to the entry of the signal, a step S7 executes the measurement of the blood flow velocity. Then, a step S8 terminates the measurement and the sequence returns to the step S1.

In the measurement, the system control unit 47 at first inserts the optical path switching mirror 34 into the optical path, whereby the light beam entering from the spot image P on the pupil Ep of the eye to be examined E is received by the photomultipliers 46a, 46b, and the output signals thereof are fetched and processed in the system control unit 47 to obtain maximum frequency shifts $|\Delta fmax1|$ and $|\Delta fmax2|$.

Since the incident light in this state comes from the spot image P which is sufficiently displaced from the received measuring light beams Da, Db, the maximum velocity is normally given by the following equation (1):

$$Vmax=\{\lambda/(n\cdot\alpha)\}\cdot ||\Delta fmax1|-|\Delta fmax2|| \qquad (1)$$

wherein $\lambda$ is the wavelength of the measuring light beam, n is the refractive index of the measured region, and $\alpha$ is the angle formed by the measuring light beam and the received light beam.

However, depending on the position of the vessel Ev on the eye fundus Ea, the true maximum velocity Vmax may have to be determined by the following equation (2):

$$Vmax=\{\lambda/(n\cdot\alpha)\}\cdot ||\Delta fmax1|+|\Delta fmax2|| \qquad (2)$$

After a temporary measurement is executed in this state and the maximum velocity Vmax is calculated by the equation (1), the optical path switching mirror 34 is retracted from the optical path by the system control unit 47, and the measurement is executed again by introducing the light beam from the spot image P' on the pupil Ep of the eye to be examined E.

The center of the spot image P' is so positioned on the pupil Ep, as shown in FIG. 7, as to be on a line passing through the center of the other spot image P and parallel to the line connecting the centers of the received measuring light beams Da, Db. In the present embodiment, in particular, the spot image P' is so selected that the distance between the spot images P and P' is larger than the distance between the centers of the received measuring light beams Da, Db and that a line connecting the middle points of the above-mentioned two lines is perpendicular to these two lines.

After the incident light is switched from the spot image P to the thus selected spot image P', the system control unit 47 again fetches the signals from the two photomultipliers 46a, 46b to calculate the respective maximum frequency shifts|Δfmax1'| and |Δfmax2'|, and obtains the maximum velocity Vmax according to the equation (1). Through the comparison of the two maximum velocities Vmax and Vmax', the system control unit 47 determines an appropriate incident direction of the light beam for obtaining the true maximum velocity, then executes appropriate optical path switching based on the thus obtained information, and continues the measurement by repeating the calculation of the maximum velocity Vmax or Vmax' at a suitable interval. The maximum blood flow velocity Vmax or Vmax' obtained in this manner is displayed on the LED 111, and the measurement of the vessel Ev to the right of the disc is thus completed.

In the present embodiment there has been explained a tracking operation by selecting a part of a vessel Ev, but it is also possible to select the target region of tracking from each of plural vessels Ev or a characteristic region other than the vessel, such as a disc as the target region of tracking. Furthermore, the tracking may be executed, instead of selecting a characteristic region as the target, by selecting a broad area of the eye fundus Ea as the target.

As explained in the foregoing, the ophthalmic apparatus of the present invention automatically and promptly controls the gain of the detection means after the preparation for the tracking operation to the selected position but prior to the execution of tracking, thereby enabling measurement with the minimum light irradiation to the examinee without the cumbersome gain adjusting operation and without requiring a long time. Also, in case the power of the tracking light is changed between before and during the tracking operation in order to reduce the energy of the tracking light given to the examinee, the gain of the detection means can be controlled in consideration of such change.

In the following there will be explained an apparatus comprising illumination means for illuminating an area including a specified target region of the eye fundus; image taking means for taking the image of the specified region, thereby outputting an image signal; process condition determination means for determining the process condition, based on the output signal from the image taking means or a signal in the vicinity of the specified region contained in the result of processing of such an output signal; region extracting means for extracting the specified region according to the process condition determination means; and auto tracking means for automatically tracking the specified region based on the output of the region extracting means.

Also, a next embodiment provides an ophthalmic inspecting apparatus comprising illumination means for illuminating an area including a specified target region of the eye fundus; image taking means for taking the image of the specified region, thereby outputting an image signal; process condition determination means for determining the process condition, based on the output signal from the image taking means or a signal in the vicinity of the specified region contained in the result of processing of such an output signal; region extracting means for extracting the specified region according to the process condition determination means; and auto tracking means for automatically tracking the specified region based on the output of the region extracting means.

Figure 14:
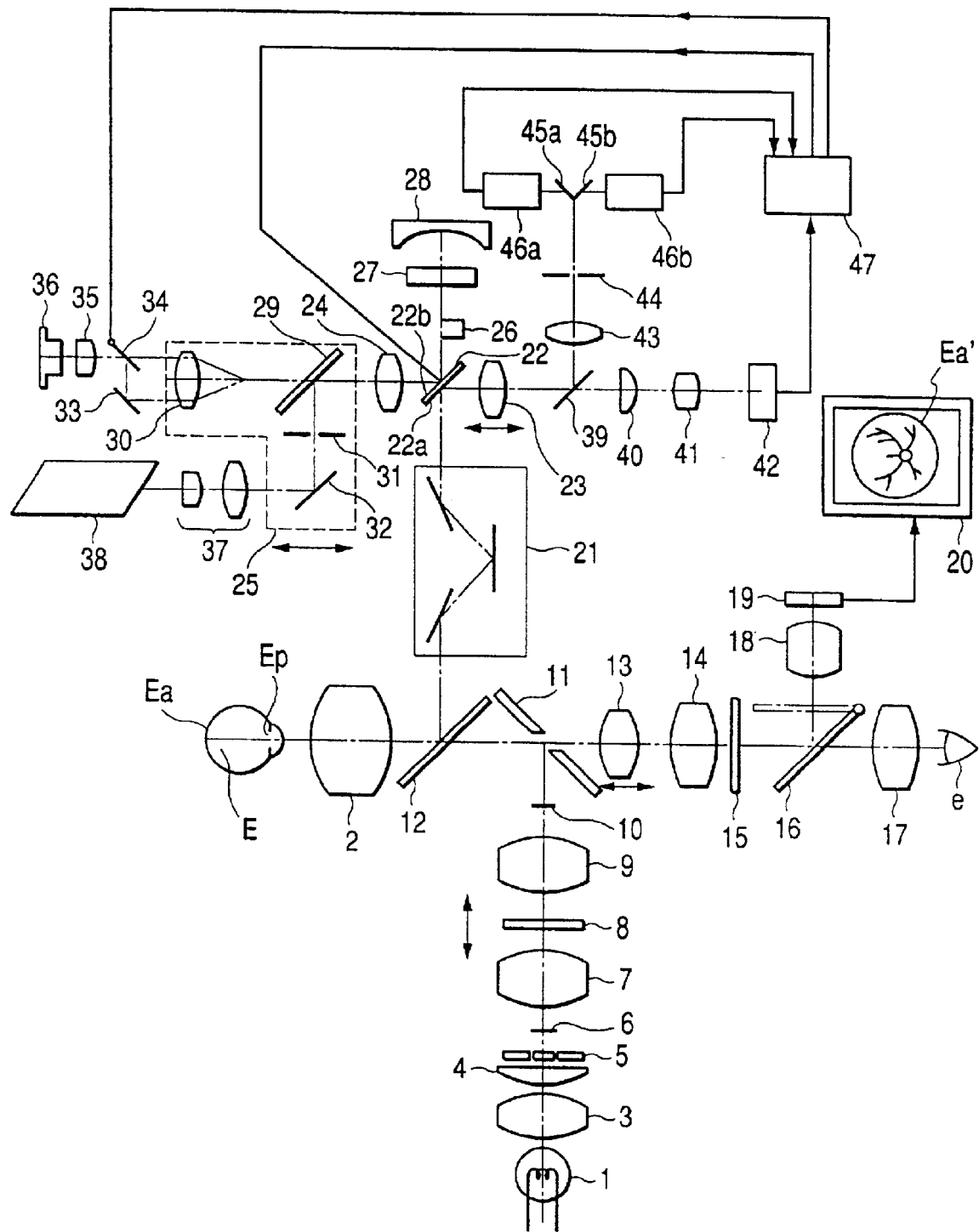
FIG. 14 is a view showing the configuration of another embodiment.

FIG. 14 shows the configuration of an eye fundus blood flow meter constituting an embodiment of the present invention, in which, on an illumination light path from an observation light source 1, composed, for example, of a tungsten lamp emitting white light, to an objective lens 2 opposed to an eye to be examined E, there are, in succession, provided a condenser lens 3, a field lens 4 with a band-pass filter transmitting, for example, only the yellow wavelength region, a ring slit 5 substantially conjugate with the pupil Ep of the eye to be examined E, a light shield member 6 substantially conjugate with the lens of the eye to be examined E, a relay lens 7, a transmissive liquid crystal panel 8 rendered movable along the optical path and serving as a fixation target display element, a relay lens 9, a light shield member 10 conjugate with the vicinity of the cornea of the eye to be examined E, a holed mirror 11, and a band-pass filter 12 transmitting light of the yellow wavelength region and reflecting the light of most of other wavelength regions.

Behind the holed mirror 11 there is provided an eye fundus observing optical system, which is provided, in succession in the path to the observing eye e, a focusing lens 13 movable along the optical path, a relay lens 14, a scale plate 15, an optical path switching mirror 15 insertable into and retractable from the optical path, and an eyepiece lens 17. In an optical path in the direction of reflection of the optical path switching mirror 16 when it is inserted into the optical path, there are provided a television relay lens 18 and a CCD camera 19 whose output is supplied to a liquid crystal monitor 20.

Also, in an optical path in the direction of reflection of the band-pass filter 12, there are provided an image rotator 21 and a galvanometric mirror 22 polished on both faces and having a rotary axis perpendicular to the plane of drawing, and in the direction of reflection of the lower reflective face 22a of the galvanometric mirror 22 provided is a second focus lens 23 movable along the optical path, while, in the direction of reflection of the upper reflective face 22b, there are provided a lens 24 and a focusing unit 25 movable along the optical axis. The front focal plane of the lens 24 is conjugate with the pupil Ep of the eye to be examined E and the galvanometric mirror 22 is positioned on such a focal plane.

Behind the galvanometric mirror 22 there are provided an optical path length compensating semi-circular plate 26, a black spot plate 27 having a light shield region in the optical path, and a concave mirror 28 positioned in a concentric manner on the optical axis, thereby constituting a relay optical system for guiding the light beam, which is not reflected by the lower reflective face 22a of the galvanometric mirror 22, to the upper reflective face 22b thereof. The optical path length compensating semicircular plate 25 is designed to compensate for the aberration, in the vertical direction of the drawing, resulting from the thickness of the galvanometric mirror 22 between the upper reflective face 22b and the lower reflective face 22a thereof, and functions only in the optical path toward the image rotator 21.

In the focusing unit 25 there are provided, on the optical path of the lens 24, a dichroic mirror 29 and a condenser lens 30, and, on an optical path in the direction of reflection of the dichroic mirror 29 there are provided a shaping mask 31 and a mirror 32. The focusing unit 25 is rendered integrally movable in a direction indicted by an arrow, along the optical path.

On an optical path at the entrance side of the condenser lens 30, there are provided in a parallel manner a fixed mirror 33 and an optical path switching mirror 34 retractable from the optical path, and, on an optical path at the entrance side of the optical path switching mirror 34, there are provided a collimating lens 35 and a measuring laser diode 36 emitting coherent light, such as light of a red color. Furthermore, on an optical path at the entrance side of the mirror 32 there are provided a beam expander 37 composed, for example, of a cylindrical lens, and a tracking light source 38 emitting light of a high intensity of a color, for example green, different from that of the other light source.

On an optical path behind the second focusing lens 23, there are in succession provided a dichroic mirror 39, a field lens 40, a magnifying lens 41 and a one-dimensional CCD 42 with an image intensifier, thereby constituting a vessel detection system. Also, on an optical path in the direction of reflection by the dichroic mirror 39, there are provided an imaging lens 43, a confocal diaphragm 44 and paired mirrors 45a, 45b substantially conjugate with the pupil Ep of the eye to be examined E, and, in the directions of reflection by the paired mirrors 45a, 45b, there are respectively provided photomultipliers 46a, 46b to constitute measuring light receiving optical systems.

All the optical paths are illustrated on a same plane for the purpose of simplicity, but the optical path from the laser diode 36 to the mask 31, the measuring optical path at the exit side of the tracking light source 38 and the reflection optical paths of the paired mirrors 45a, 45b are in fact perpendicular to the plane of the drawing.

For controlling the entire apparatus there is provided a system control unit 47, to which are supplied the outputs of the one-dimensional CCD 42 and of the photomultipliers 46a, 46b, and the output of the system control unit 47 is supplied to the galvanometric mirror 22 and the optical path switching mirror 34.

Figure 15:
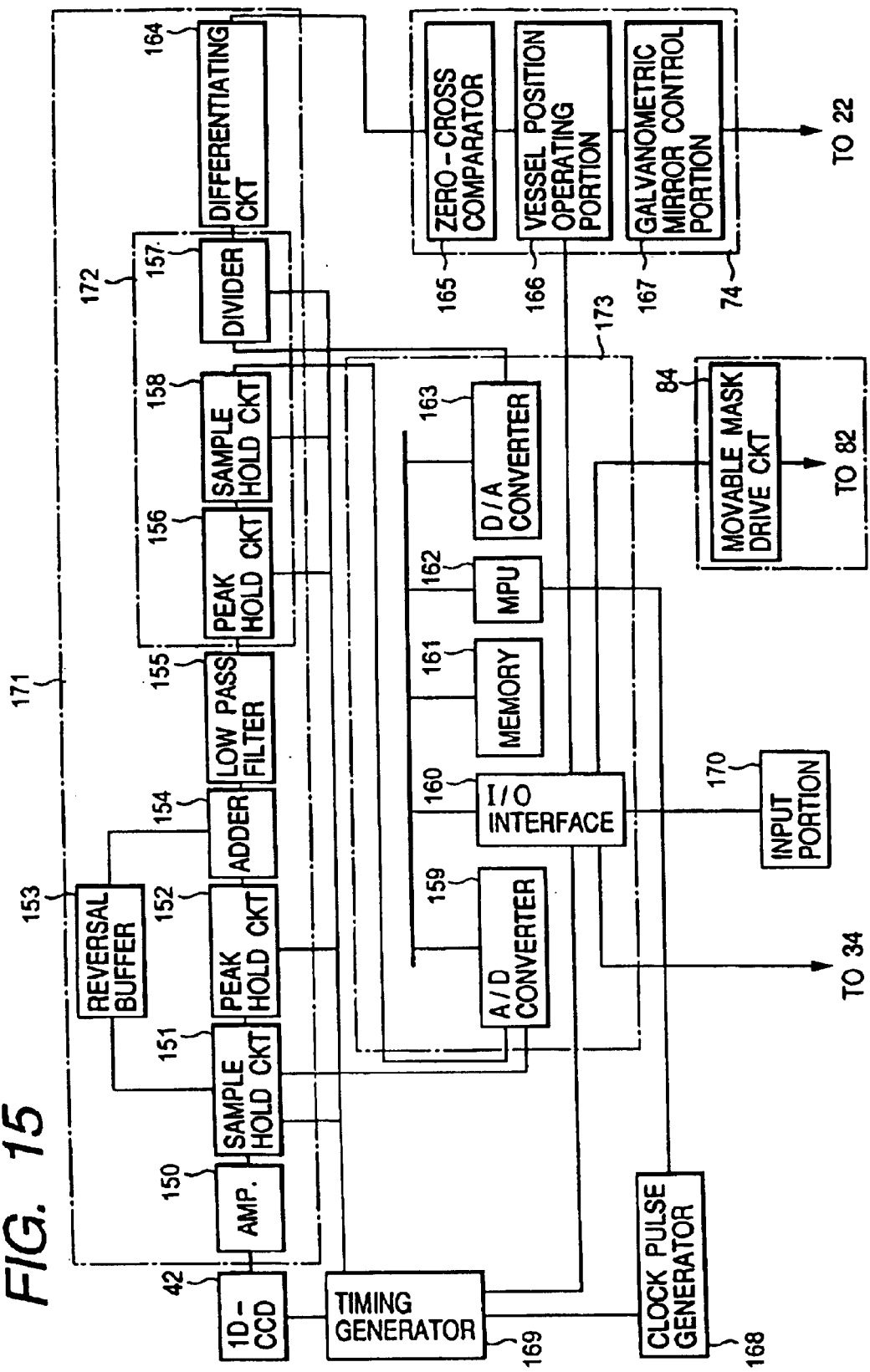
FIG. 15 is a view showing the configuration of a block circuit in the system control unit.

FIG. 15 shows the configuration of the system control unit 47, in which the output of the one-dimensional CCD 42 is connected in succession to an amplifier 150 and a sample hold circuit 151, whose output is connected to a peak hold circuit 152, and an inverting buffer 153. The outputs of the peak hold circuit 152 and the inverting buffer 153 are connected to an addition circuit 154, whose output is supplied to a low-pass filter 155. The output thereof is connected to a peak hold circuit 156 and a division unit 157, The output of the peak hold circuit 156 is supplied through a sample hold circuit 158 to an A/D converter 159.

The A/D converter 159 is connected, through a bus line, to an I/O interface 160, a memory 161, an MPU 162 and a D/A converter 163, and the output of the D/A converter 163 is connected to a differentiation circuit 164, and, through a zero-cross comparison unit 165, to a vessel position calculating unit 166, which also receives the output of the I/O interface 160 and whose output is connected through a galvanometric mirror control unit 167 to the galvanometric mirror 22.

Also, the output of a clock pulse generator 168 is connected to the MPU 162 and a timing generator 169, whose output is connected to the one-dimensional CCD 42, the sample hold circuits 151, 158, the peak hold circuits 152, 156 and the division unit 157. Also the output of the I/O interface 160 is connected to the optical path switching mirror 34, and the output of an input unit 170 is connected to the I/O interface 160. A movable mask drive circuit 84 is connected to a movable mask 82.

A vessel region extracting unit 171 is constituted by the amplifier 150, sample hold circuits 151, 158, peak hold circuits 152, 156, inverting buffer 153, addition circuit 154, division unit 157 and differentiation circuit 164, and an AGC (automatic gain control) unit 172, which is constituted by the peak hold circuit 156, the division unit 157 and the sample hold circuit 158. Also, a process condition determination unit 173 is constituted by the A/D converter 159, the I/O interface 160, the memory 161, the MPU 162 and the D/A converter 163, and an auto tracking control unit 174 is constituted by the zero-cross comparison unit 165, the vessel position calculation unit 166, and the galvanometric mirror control unit 167.

Figure 16:
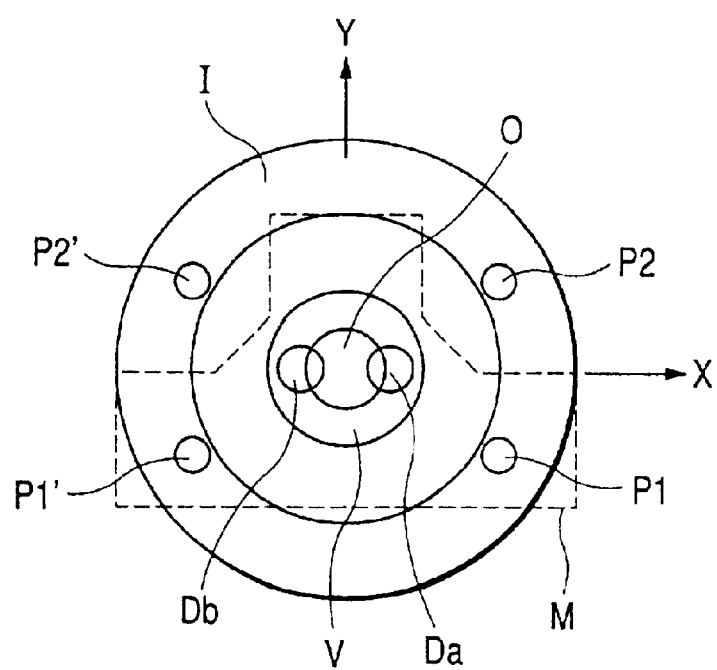
FIG. 16 is a schematic view showing the arrangement of optical beams on the pupil Ep.

FIG. 16 shows the arrangement of the light beams on the pupil Ep of the eye to be examined E, including an area I illuminated with the yellow illuminating light and corresponding to an image of the ring slit 5, an eye fundus observing light beam O showing an image of the aperture of the holed mirror 11, a measuring/received light beam V showing an image of the effective area of the upper and lower reflective faces of the galvanometric mirror 22, and two received measuring light beams Da, Db showing images of the paired mirrors 45a, 45b. There are also shown entrance positions P2, P2' of the measuring light, selected by the switching of the optical path switching mirror 34, and a chain-lined area M indicating an image of the lower reflective face 22a of the galvanometric mirror 22.

The white light emitted from the observing light source 1 is transmitted by the condenser lens 3. Then, light of the yellow wavelength region only is transmitted by the field lens 4 with the band-pass filter, is further transmitted by the ring slit 5, the light shield member 6 and the relay lens 7, illuminates the transmissive liquid crystal panel 8 from the rear side, is further transmitted by the relay lens 9 and the light shield member 10, and is reflected by the holed mirror 11. Thus, light of the yellow wavelength region only is transmitted by the band-pass mirror 12 and the objective lens 2 and is focused as an image I of the eye fundus illuminating light beam on the pupil Ep of the eye to be examined E, thus uniformly illuminating the eye fundus Ea.

In this state, the transmissive liquid crystal panel 8 displays a fixation target which is projected by the illuminating light onto the eye fundus Ea of the eye to be examined E and is presented thereto as a fixation target image. The light shield members 6, 10 serve to separate the eye fundus illuminating light and the eye fundus observing light at the front eye region of the eye to be examined E, and the shape of these components is not critical as long as a suitable light shielding area can be formed.

The light reflected by the eye fundus Ea returns on the same optical path and is taken out, from the pupil Ep, as an eye fundus observing light beam, which is guided through the central hole of the holed mirror 11, the focusing lens 13 and the relay lens 14, is then focused as an eye fundus image Ea' by the scale plate 15 and reaches the optical path switching mirror 16.

When the optical path switching mirror 16 is retracted from the optical path, the observing eye e can observe the eye fundus image Ea' through the eye piece lens 17, but, when the optical path switching mirror 16 is inserted into the optical path, the eye fundus image Ea' focused on the scale plate 15 is refocused on the CCD camera 19 through the television relay lens 18 and is displayed on the liquid crystal monitor 20. The alignment of the apparatus is made under the observation of the eye fundus image Ea' either through the eyepiece lens 17 or the liquid crystal monitor 20.

The measuring light, emitted from the laser diode 36, is collimated by the collimating lens 35 and, if the optical path switching mirror 34 is inserted in the optical path, is reflected by this mirror 34 and the fixed mirror 33 to pass through the lower part of condenser lens 30, but, if the optical path switching mirror 34 is retracted from the optical path, it directly passes through the upper part of condenser lens 30, thus being transmitted by the dichroic mirror 29.

On the other hand, the tracking light emitted from the tracking light source 38 is expanded in beam diameter with different magnifications in the vertical and horizontal directions by the beam expander 37, then is reflected by the mirror 32, is shaped into a desired shape by the shaping mask 31, is further reflected by the dichroic mirror 29 and is superposed by the condenser lens 30 with the measuring light, which is focused into a spot at a position conjugate with the center of the aperture of the mask 31.

The measuring light and the tracking light mutually superposed are transmitted by the lens 24, reflected by the upper reflective face 22b of the galvanometric mirror 22, transmitted by the black spot plate 27, reflected by the concave mirror 28, again transmitted by the black spot plate 27 and the optical path length correcting semicircular plate 26, and are returned toward the galvanometric mirror 22.

By the function of the relay optical system, which is positioned above the galvanometric mirror 22 and which forms the image of the upper reflective face 22b and the lower reflective face 22a of the galvanometric mirror 22 with a magnification of −1, the measuring light and the tracking light, reflected at either position P or P' located as shown in FIG. 16 at the rear side of the image M of the dichroic mirror 22, are returned to a position P2 or P2' corresponding to the recessed portion of the galvanometric mirror 22, thus being directed to the image rotator 21 without being reflected by the galvanometric mirror 22. After passing the image rotator 21, the measuring light and the tracking light are deflected by the band-pass filter 12 toward the objective lens 2 and projected onto the eye fundus Ea of the eye to be examined E.

Thus, the measuring light and the tracking light are reflected by the upper reflective face 22b of the galvanometric mirror 22, and, in the returning path, they enter the galvanometric mirror 22 in a state deviated from the optical axis of the objective lens 2, whereby these lights are focused as a spot image P2 or P2' on the pupil Ep as shown in FIG. 3 and illuminate the eye fundus Ea in a spot shape.

The light scattered and reflected at the eye fundus Ea is condensed by the objective lens 2, is then reflected by the band-pass filter 12, transmitted by the image rotator 21, reflected by the lower reflective face 22a of the galvanometric mirror 22, and transmitted by the second focusing lens 23, and the measuring light and the tracking light are separated by the dichroic mirror 39. The tracking light is transmitted by the dichroic mirror 39, and is focused by the field lens 40 and the imaging lens 41 on the one-dimensional CCD 42.

A part of the measuring and tracking lights scattered and reflected on the eye fundus Ea is transmitted by the band-pass mirror 32 and guided to the eye fundus observing optical system positioned behind the holed mirror 11, wherein the tracking light is focused on the scale plate 15 as a rod-shaped indicator T, while the measuring light is focused as a spot at the center of the indicator T. These images can be observed, together with the eye fundus image Ea' and the fixation target image, through the eyepiece lens 17 or the liquid crystal monitor 20. In this state, an unrepresented spot image is superposed at the center of the indicator T, which can be moved one-dimensionally on the eye fundus Ea by an operation member, such as the operation rod of the input unit 170.

At first the examiner executes focusing of the eye fundus image Ea'. By the adjustment of a focusing knob of the input means 170, the transmissive liquid crystal panel 8, the focusing lenses 13, 23 and the focusing unit 25 are moved in mutual linkage, by unrepresented drive means, along the optical axis. When the eye-fundus image Ea' is focused, all the transmissive liquid crystal panel 8, the scale plate 15, the one-dimensional CCD 42 and the confocal diaphragm 44 become conjugate with the eye fundus Ea. Observing the focus state on the eye fundus image Ea', the examiner sets the depth of the vessel Ev to be measured, and executes focusing of the eye fundus image Ea'.

After the focusing operation, the examiner changes the observation area by guiding the visual axis of the eye to be examined E, and manipulates the input unit 170 to move the target vessel Ev to a suitable position. The system control unit 47 drives a control circuit for controlling the transmissive liquid crystal panel 8 to move the fixation target image. Then, the examiner manipulates the operation rod of the input unit 170 to rotate the indicator T in such a manner that it becomes perpendicular to the longitudinal direction of the target vessel Ev. The system control unit 47 drives a control circuit for controlling the image rotator 21, thereby driving the image rotator 21 and rotating the indicator T.

After confirming the tracking, the examiner presses in the measuring switch of the input unit 170 to initiate the measurement. The measuring light is reflected by the dichroic mirror 39, is then transmitted through the aperture of the confocal diaphragm 44, is reflected by the paired mirrors 45a, 45b and received by the photomultipliers 46a, 46b, whose outputs are supplied to the system control unit 47 and are subjected to frequency analysis to determine the blood flow velocity on the eye fundus Ea.

Figure 17:
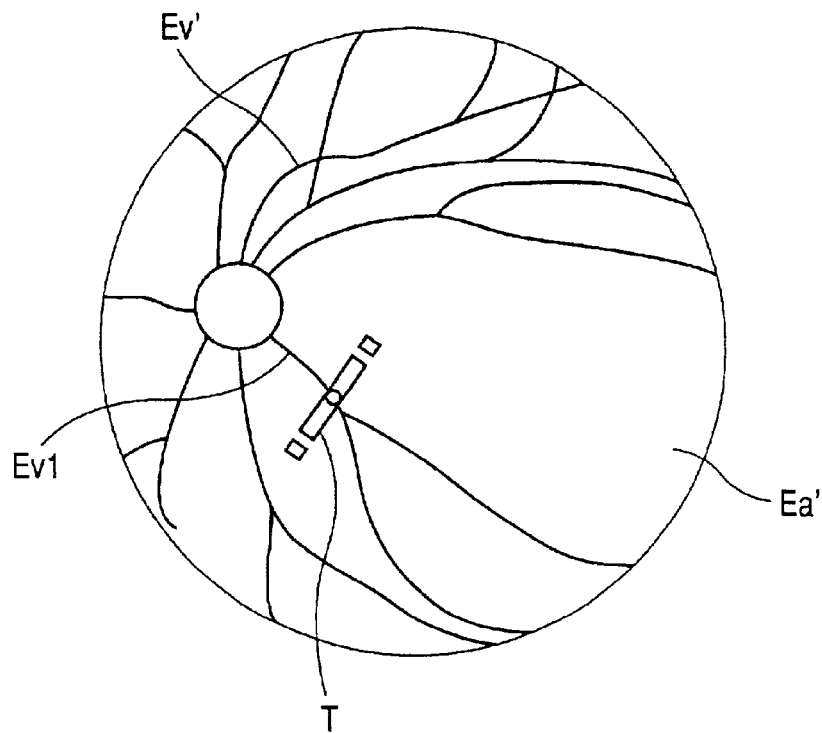
FIG. 17 is a schematic view showing the image of an observed eye fundus.

In case vessels Ev are absent around the vessel Ev1 to be tracked as shown in FIG. 17, in response to the start of the tracking operation by the examiner, the vessel image Ev' taken by the one-dimensional CCD 42 is read at a timing generated by the timing generator 169 and is amplified by the amplifier 150. The output signal thereof is subjected to sample holding in the sample hold circuit 151 at a timing generated by the timing generator 169. Since the portion of the vessel Ev is dark while the surrounding area is light, the output signal assumes a form as shown in FIG. 18D, wherein a portion of the high output level indicates a light region.

The output signal of the sample hold circuit 51 is entered into the peak hold circuit 152, which executes peak holding only during an L-level period generated by the timing generator 169 as shown in FIG. 18A, but merely transmits the input signal in other periods. The output of the peak hold circuit 152 and a signal obtained by inverting, by the inverting buffer 153, the output of the sample hold circuit 151 are supplied to and added in the addition circuit 154 whereby a vessel image signal alone is extracted as shown in FIG. 18E. The output of the addition circuit 154 is supplied to the low-pass filter 155 to eliminate the high frequency components as shown in FIG. 18G.

The output of the low-pass filter is supplied to the peak hold circuit 156, which executes peak holding only during an L-level period, as shown in FIG. 18B, for supply to the sample hold circuit 158. The sample hold circuit 158 executes a sampling operation in an L-level period as shown in FIG. 18C and a holding operation in an H-level period. The output signal of the sample hold circuit 158 is shown, together with the output signal of the low-pass filter 155, in FIG. 18F, and enters into the A/D converter 159 for conversion into digital data, which are processed in the MPU 162 and released from the D/A converter 163 as an AGC gain for vessel position detection in the next sampling cycle.

FIGS. 18A to 18I show the signal wave forms in case the signal level entered from the MPU 162 to the A/D converter 159 is set to the D/A converter 163. The output wave form thereof is supplied as the AGC gain for the vessel position detection while that of the low-pass filter 155 is supplied as the tracking signal, to the division unit 157, which executes a calculation (output signal of low-pass filter 155)÷(output signal of D/A converter 163) and executes auto gain control for the vessel position detection by the sampling of a period on the signal of the vessel to be tracked.

The output signal, shown in FIG. 18H, of the division unit 157 is differentiated by the differentiation circuit 164, whose output is entered into the zero-cross comparison unit 165 and is compared therein with ca. 0 V. The obtained signal is outputted as the vessel position signal shown in FIG. 18I. This vessel position signal is compared, in the vessel position calculation unit 166, with a tracking center position signal outputted from the I/O interface 160, thereby outputting the amount of displacement of the vessel closest to the center of tracking, to the galvanometric mirror control unit 167, which in response drives the galvanometric mirror 22 so as to compensate for this amount of displacement.

Figure 19:
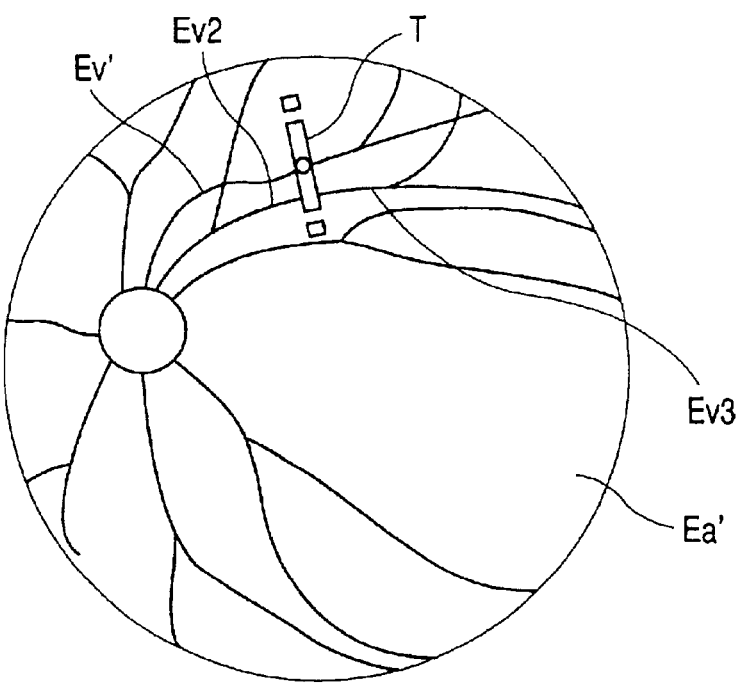
FIG. 19 is a schematic view showing the image of an observed eye fundus.

In the following there will be explained, with reference to output wave forms shown in FIGS. 20A to 20I, a case where a vessel Ev3 of a higher contrast is present around a vessel Ev2 to be tracked, as shown in FIG. 19. If the signal level entered from the MPU 162 to the A/D converter 159 is entered, without change, to the D/A converter 163, the displacement amount d from the tracking center of the vessel Ev2 is smaller than the displacement amount d' from the tracking center of the vessel Ev3 in a sampling cycle n=0, so that the vessel position calculation unit 166 outputs the displacement amount d of the vessel closest to the tracking center, to the galvanometric mirror control unit 167, which drives the galvanometric mirror 22 so as to compensate for this displacement amount d, whereby, in a sampling cycle n=1, the image of the vessel Ev2 is taken at the approximate center of tracking.

In a sampling cycle n=1, however, the AGC for the vessel position detection is controlled with a gain based on the vessel Ev3, whereby the signal of the vessel Ev2 is normalized to a small value as shown in FIG. 20H and the output of the zero-cross comparison unit 165 becomes unstable. On the other hand, the image signal of the vessel Ev3 is given an appropriate AGC, whereby the output of the zero-cross comparison unit 165 becomes stable. Consequently, the vessel position calculation unit 166 may judge the vessel position signal of the vessel Ev3 as the displacement amount of the vessel closest to the tracking center whereby the tracking operation may be applied to the vessel Ev3.

Figure 21:
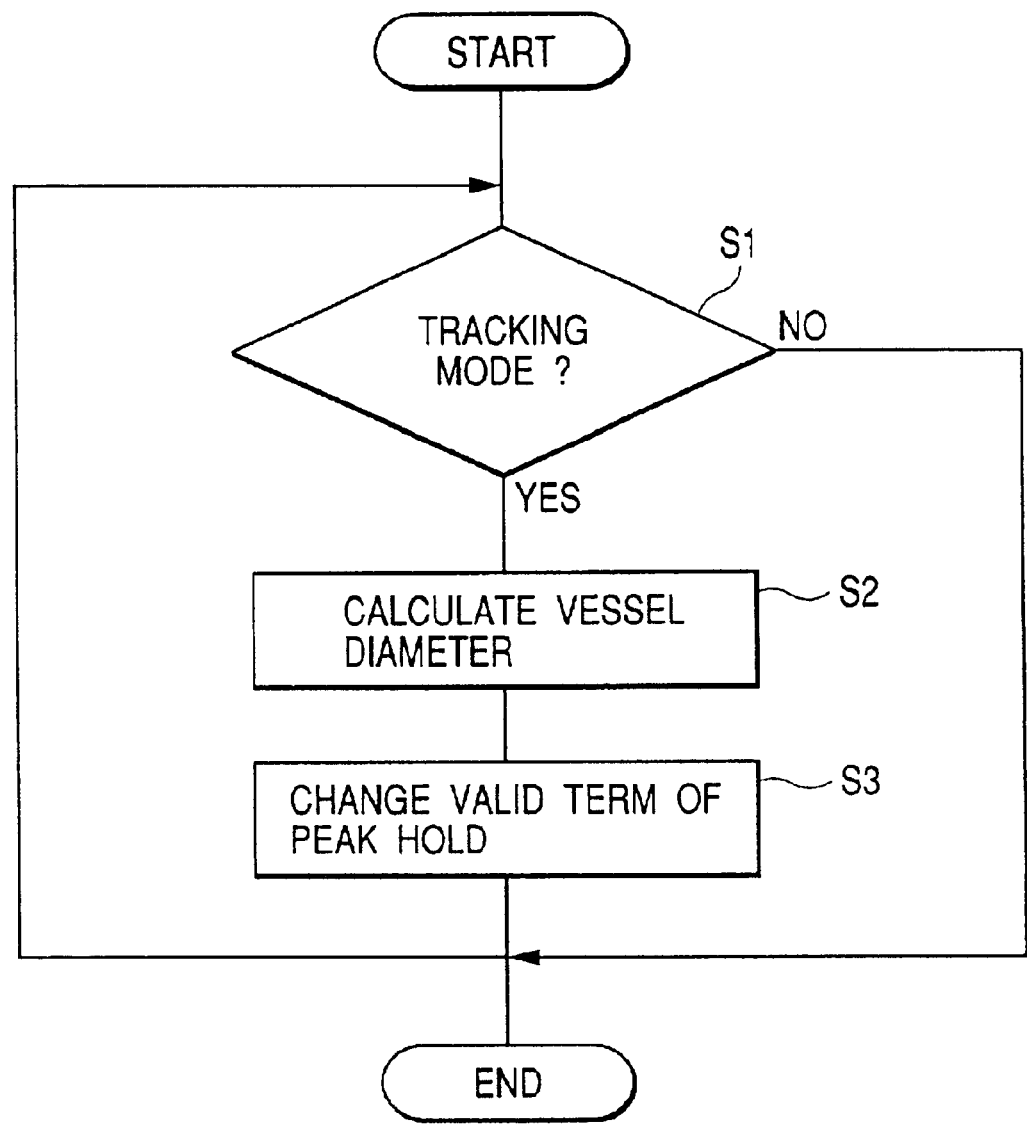
FIG. 21 is a flow chart.
Figure 22:
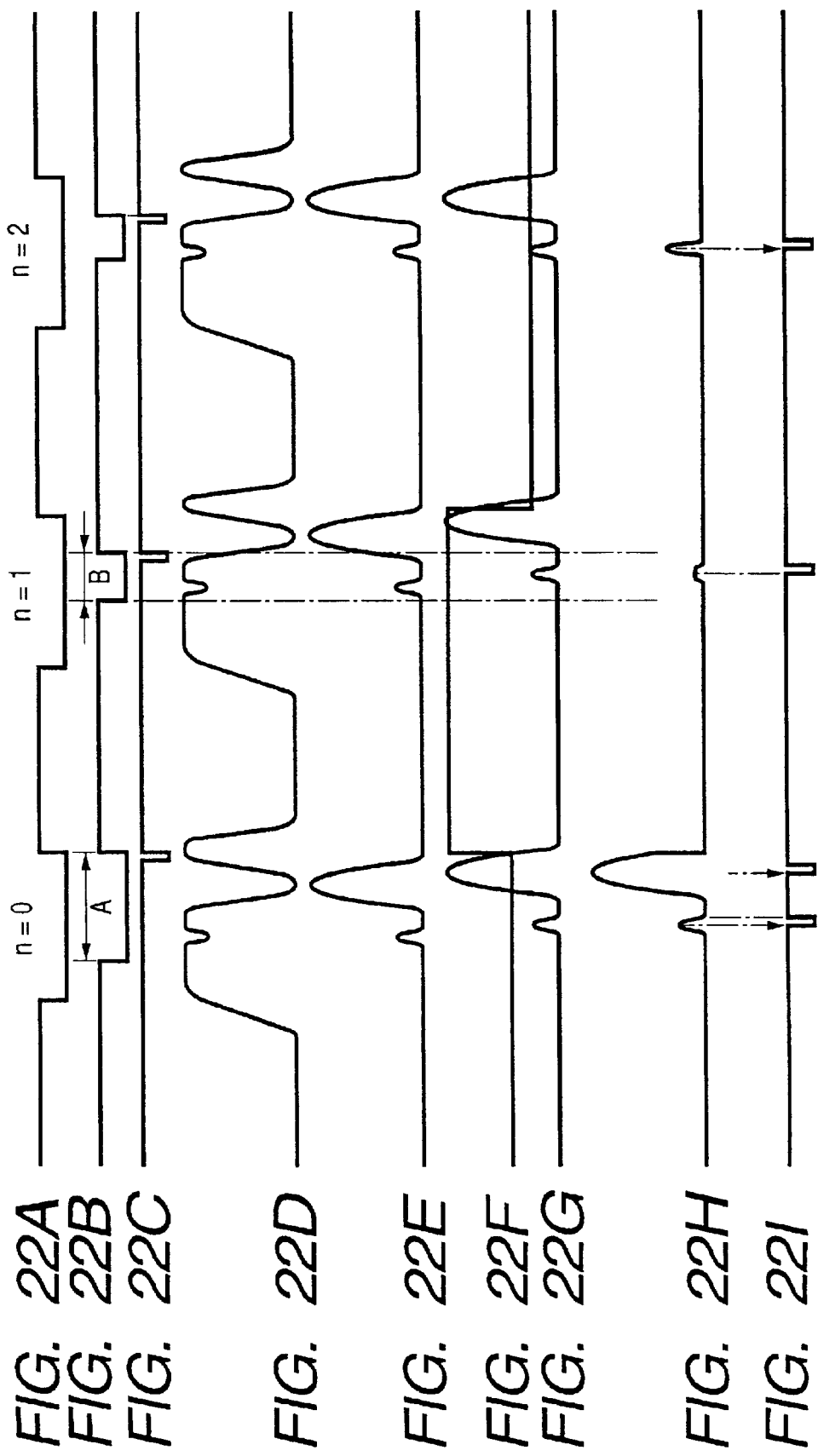
FIGS. 22A, 22B, 22C, 22D, 22E, 22F, 22G, 22H and 22I and FIGS. 23A, 23B, 23C, 23D, 23E, 23F, 23G, 23H, 23I and 23J are timing charts showing a tracking signal.

In order to prevent such phenomenon, the MPU 162 executes a process according to a flow chart shown in FIG. 21. A step S1 discriminates if the tracking mode is selected, and, if selected, a step S2 executes conversion of the image signal from the sample hold circuit 151 into digital data, then executes wave form analysis by the MPU 162 and calculates the diameter of the vessel closest to the tracking center in the sampling cycle n=0.

Then, in a step S3, the MPU 162 outputs a signal for varying according to the thus calculated vessel diameter, the peak hold period of the peak hold circuit 156, indicating the effective AGC range of the AGC unit 172 for the vessel position detection, to the timing generator 169 through the I/O interface 160, thereby varying the peak hold period from A to B as shown in FIGS. 22A to 22I. In the present embodiment, the effective AGC range for the vessel position detection is so varied that the peak hold period becomes about twice that of the vessel diameter.

Figure 23:
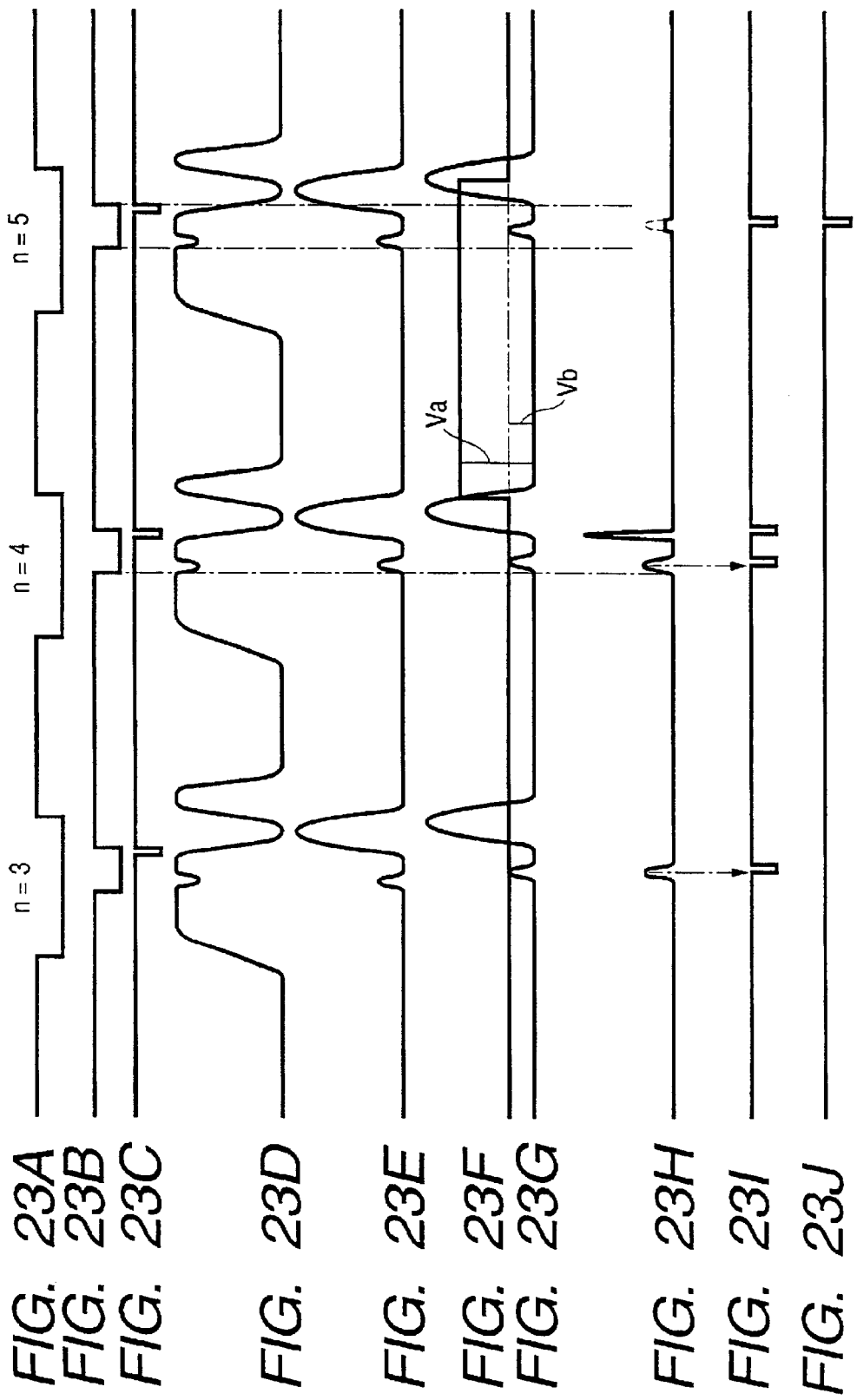

FIGS. 23A to 23J show the wave forms in the sampling cycles n=3 to 5, succeeding to the sampling cycle n=2 shown in FIGS. 22A to 22I. FIGS. 23A to 23J show a case in which the tracking is disturbed by an external perturbation in the sampling cycle n=4, and the image signal of the vessel Ev3 is introduced in the effective AGC range for the vessel position detection, namely in the period B. In the sampling cycle n=4, as shown in FIG. 23G, a part of the image signal of the vessel Ev3 is retained by the sample hold circuit 158, and entered into the A/D converter 159, whereby the AGC gain for the vessel position detection in the sampling cycle n=5 is outputted from the D/A converter 163. The AGC gain for the vessel position detection in the sampling cycle n=5 assumes a value I/Va, which is smaller than the gain I/Vb required for applying appropriate AGC to the vessel Ev2, so that the output signal for the vessel Ev2 from the zero-cross comparison unit 165 becomes unstable as shown in FIG. 23I.

Figure 24:
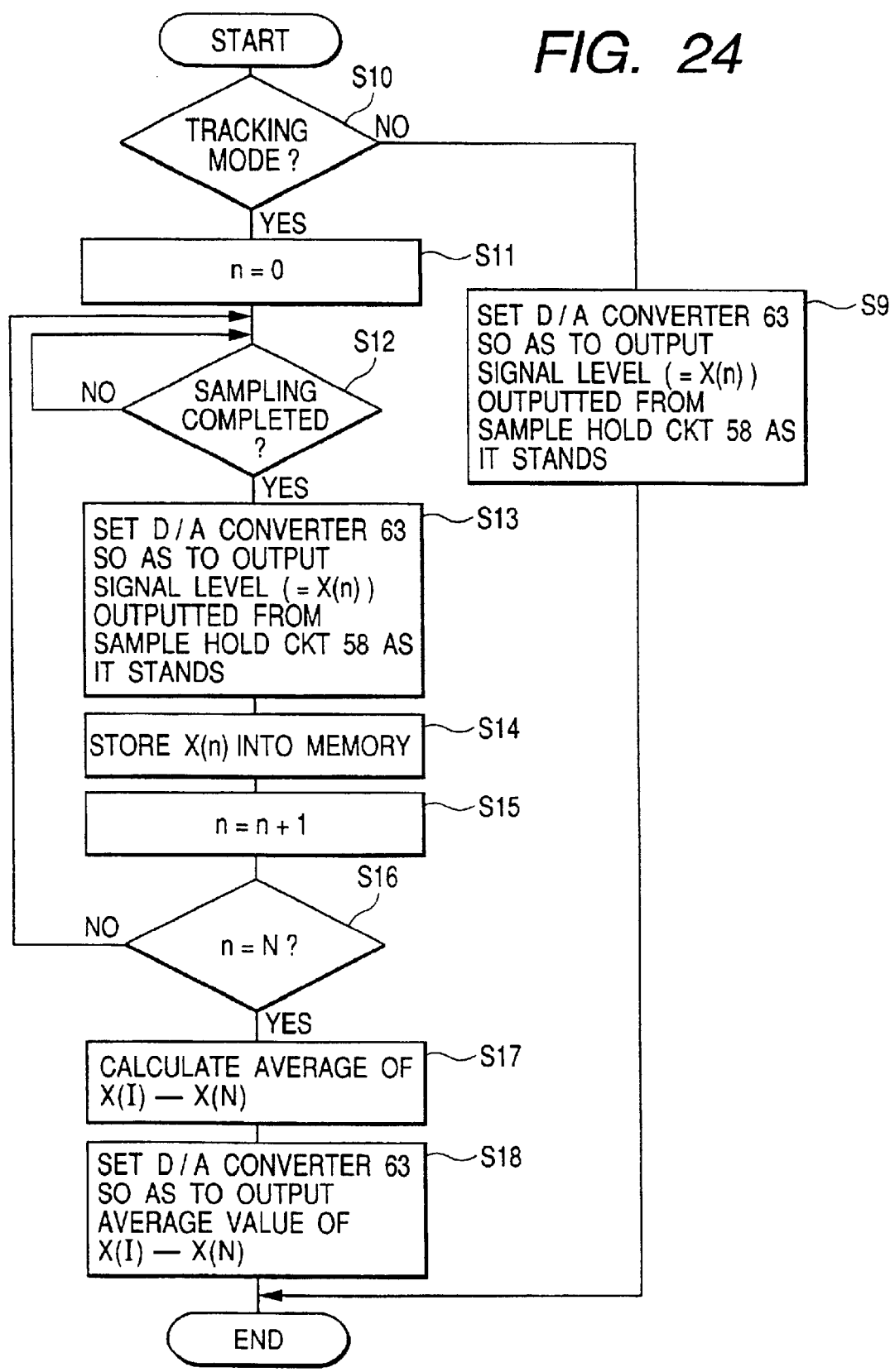
FIG. 24 is a flow chart.

Therefore, the MPU 162 executes a process according to a flow chart shown in FIG. 24. A step S10 discriminates whether the tracking mode is selected, and, if selected, a step S11 resets a counter for determining the number of samplings of the signal level outputted from the sample hold circuit 158. If the number of samplings does not exceed a predetermined value, a step S12 discriminates whether the sampling operation of the sample hold circuit 158 has been terminated, and, if terminated, a step S13 so sets the D/A converter 163 that the output signal of the sample hold circuit 158 is outputted without change, and a step S14 stores the output signal level of the sample hold circuit 158 in the memory 161. If steps S15, S16 identify that the number of samplings has reached a predetermined value, a step S17 calculates the average of the output signals from the sample hold circuit 158 and a step S18 so sets the D/A converter 163 as to output such an average value.

In the present embodiment, the predetermined value is selected as n=3, and in the sampling cycles n=0 to n=3, the output signal of the sample hold circuit 58 is outputted without change, as shown in FIGS. 22A to 22I and 23A to 23J, for applying AGC for the vessel position detection. In the sampling cycle n=4 or subsequent cycles, the AGC gain supplied to the division unit 157 is fixed at I/Vb, which is an average of the sampling cycles n=1 to n=3. Even if the tracking is disturbed by an external perturbation in the sampling cycle n=4 to include the image signal of the vessel Ev3 in the effective AGC range for the vessel position detection, namely in the period B, the output signal for the vessel Ev2 from the zero-cross comparison unit 165 in the sampling cycle n=5 is stabilized as shown in FIG. 23J so that the tracking operation becomes stable.

Figure 25:
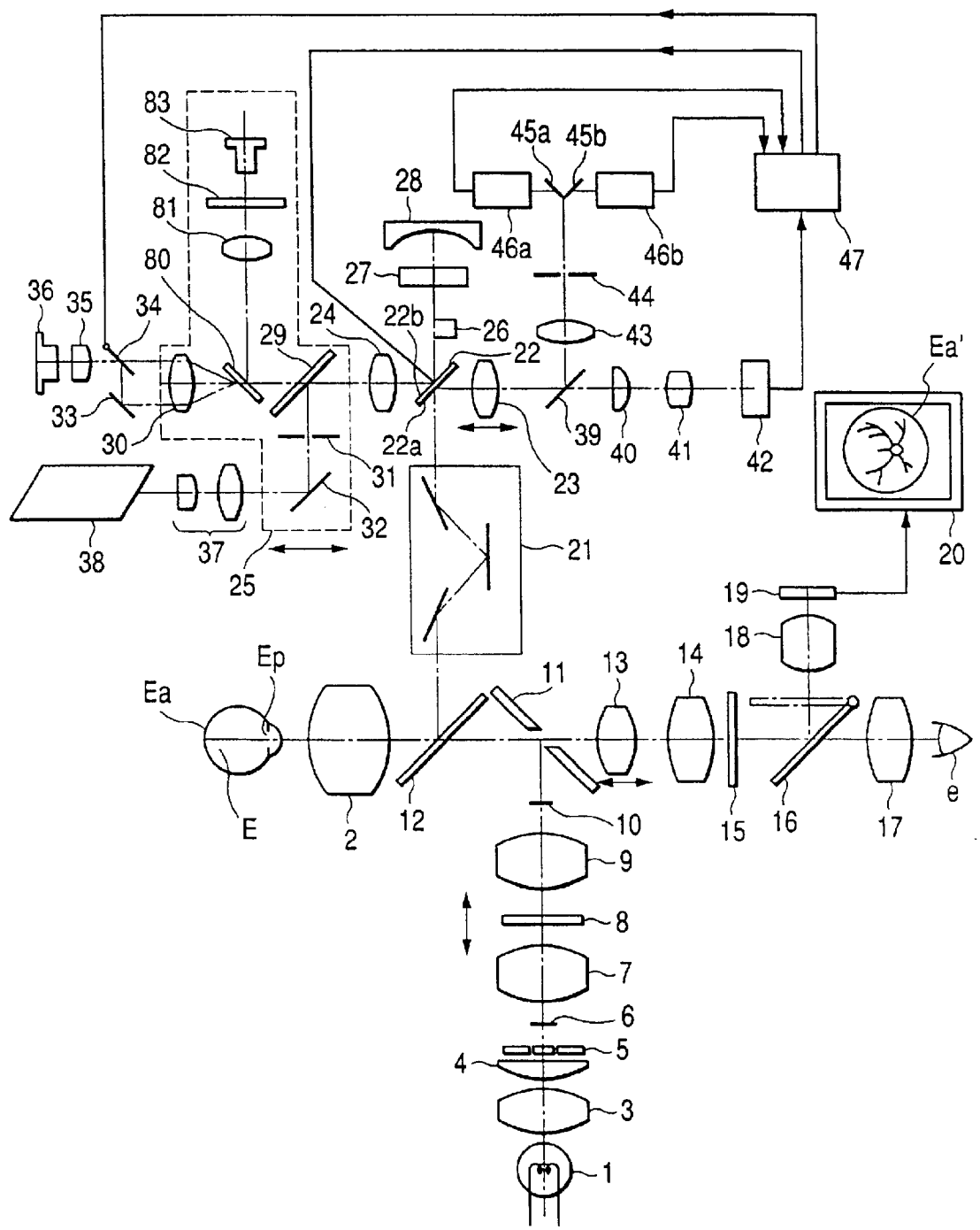
FIG. 25 is a view showing another embodiment.

FIG. 25 shows another embodiment, which is different from the first embodiment in that, in the focusing unit 25, a half mirror 80 is provided between the dichroic mirror 29 and the condenser lens 30 and that, at the entrance side of the half mirror 80, there are provided a relay lens 81, a movable mask 82 provided in a position substantially conjugate with the mask 31 and indicating the AGC range for the vessel position detection, and an LED light source 83 emitting red light. Also, the output of the I/O interface 160 of the process condition determination unit 173 shown in FIG. 15 is supplied to a movable mask drive circuit 84 for controlling the movable mask 82. Other configurations are same as those in the first embodiment, and components equivalent to those in the first embodiment are indicated by the same numbers therein.

Figure 26:
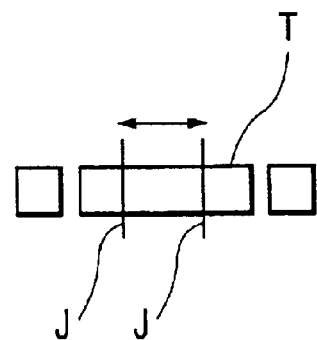
FIG. 26 is an elevation view of a tracking index.

An image of the movable mask 82 is projected, as an index mark J as shown in FIG. 26, onto the eye fundus Ea of the eye to be examined E. This index mark J indicates the effective AGC range for the vessel position detection.

Figure 27:
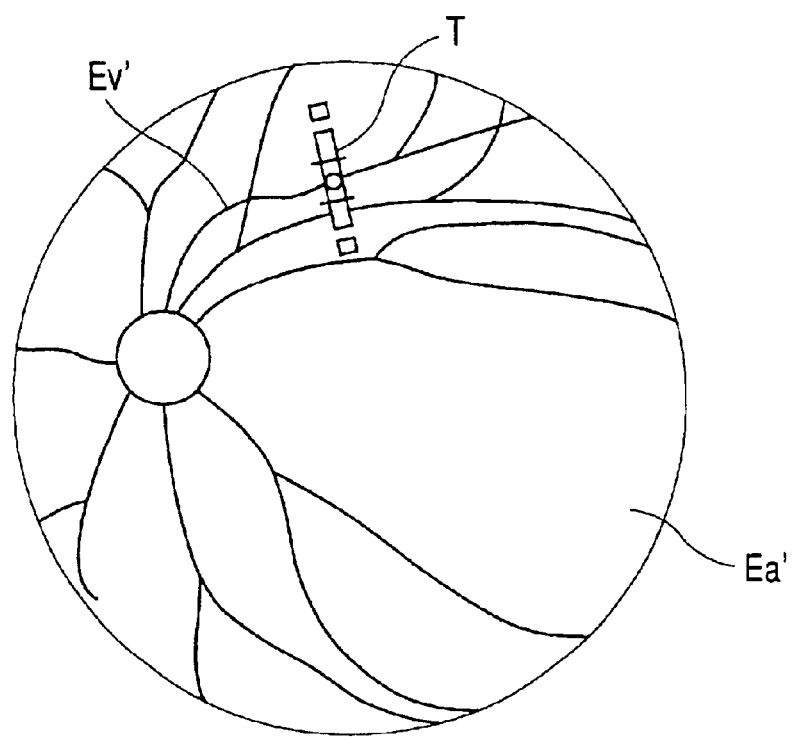
FIG. 27 is a schematic view showing the image of an observed eye fundus.

The examiner observes the state of the eye fundus image Ev' shown in FIG. 27, and, if the tracking operation is judged difficult, for example, because the vessel to be tracked has a low contrast; or is thin, the examiner manipulates the input unit 170 to manually change the effective AGC range for the tracking operation. This information is supplied through the I/O interface 160 to the MPU 162, which in response varies the peak hold period of the peak hold circuit 156, representing the effective AGC range for the vessel position detection, thereby controlling the movable mask drive circuit 84 to move the movable mask 82, whereby the index mark J or the image of the movable mask 82 is moved as indicated by an arrow in FIG. 26.

Also, in case of an automatic change of the AGC range of the tracking operation in the first embodiment, the index mark J may be projected onto the eye fundus Ea of the eye to be examined E. In this case the index mark J moves in linkage with the AGC range of the tracking operation. It is also possible to combine the configuration of the first embodiment for automatic change and that of the second embodiment for manual change.

As explained in the foregoing, the ophthalmic inspecting apparatus of the present invention is capable of executing an AGC process for the vessel position detection in a range narrower than the effective range of the tracking light and a wave form processing for normalizing the vessel image signal, by determining the processing condition based on the signal in the vicinity of the specified region and extracting the specified region for automatic tracking, whereby the tracking operation can be achieved in a stable manner on a thin vessel.

Also the ophthalmic inspecting apparatus of the present invention is capable, by determining the processing condition based on the signal in the vicinity of the specified region, displaying the result on display means and extracting the specified region for automatic tracking, of varying the effective AGC range for the vessel position detection in the tracking operation of the vessel in the eye to be examined, whereby the tracking operation can be achieved in a stable manner even on a vessel of a lower contrast when two vessels are positioned mutually close.

What is claimed is:

1. An ophthalmic apparatus comprising:

illumination means for illuminating an eye fundus area including a specified target area;

image taking means for taking the image of the eye fundus area and thereby outputting an image signal;

signal processing means for processing and normalizing the image signal, based on a condition determined in accordance with the outputted image signal from said image taking means;

position determination means for determining the position of the target area based on an output of said signal processing means; and auto tracking means for executing automatic tracking of the position of the target area based on an output of said position determining means, wherein the signal of the target area indicates a vessel image, and said signal processing means is adapted to extract a signal of a portion of the vessel image and to execute a normalization process for varying the gain based on the signal of the portion of the vessel image.

2. An ophthalmic apparatus according to claim 1, wherein said signal processing means includes normalizing range setting means for setting an effective range of the normalization process for varying the gain, based on the signal of the portion of the vessel image.

3. An ophthalmic apparatus according to claim 2, wherein said signal processing means includes normalizing range varying means for varying a size of a region of normalizing to vary the gain, based on the signal of the portion of the vessel image.

4. An ophthalmic apparatus according to claim 3, wherein said normalizing range varying means is adapted to vary a size of a region of normalizing in accordance with a diameter of the vessel image.

5. An ophthalmic apparatus according to claim 1, wherein, in the normalization process, the gain is varied from a predetermined period after a start of automatic tracking, and is thereafter fixed.

\* \* \* \* \*

UNITED STATES PATENT AND TRADEMARK OFFICE
CERTIFICATE OF CORRECTION

PATENT NO. : 6,834,202 B2
DATED : December 21, 2004
INVENTOR(S) : Shigeaki Ono

It is certified that error appears in the above-identified patent and that said Letters Patent is hereby corrected as shown below:

Column 3,
Line 25, "after to the" should read -- after the --.

Column 13,
Line 31, "the, black" should read -- the black --.

Column 14,
Line 56, "that" should read -- so that --.

Column 19,
Line 54, "157," should read -- 157. --.

Column 23,
Line 18, "period" should read -- period A --.

Signed and Sealed this

Thirteenth Day of September, 2005

JON W. DUDAS
*Director of the United States Patent and Trademark Office*